US007635686B2

(12) United States Patent
Phillips et al.

(10) Patent No.: US 7,635,686 B2
(45) Date of Patent: Dec. 22, 2009

(54) THERAPEUTICALLY USEFUL TRIETHYLENEGLYCOL CHOLESTERYL OLIGONUCLEOTIDES

(75) Inventors: Nigel C. Phillips, Pointe-Claire (CA); Mario C. Filion, Laval (CA); Andrea C. Herréra Gayol, Westmount (CA)

(73) Assignee: Bioniche Life Sciences, Inc., Belleville, Ontario (CA)

( * ) Notice: Subject to any disclaimer, the term of this patent is extended or adjusted under 35 U.S.C. 154(b) by 222 days.

(21) Appl. No.: 10/264,280

(22) Filed: Oct. 3, 2002

(65) Prior Publication Data

US 2003/0125290 A1 Jul. 3, 2003

Related U.S. Application Data

(60) Provisional application No. 60/326,884, filed on Oct. 3, 2001.

(51) Int. Cl.
*A01N 43/04* (2006.01)
*C07H 21/04* (2006.01)
(52) U.S. Cl. ...................................... 514/44; 536/23.5
(58) Field of Classification Search ................... 514/44, 514/171; 536/22.1, 25.6, 46, 47, 48, 49
See application file for complete search history.

(56) References Cited

U.S. PATENT DOCUMENTS

| 4,958,013 | A | 9/1990 | Letsinger | |
|---|---|---|---|---|
| 6,881,381 | B1 * | 4/2005 | Asher et al. | 422/68.1 |
| 6,881,831 | B2 * | 4/2005 | Iyer et al. | 536/22.1 |
| 7,087,586 | B2 * | 8/2006 | Filion et al. | 514/44 |
| 2001/0041681 | A1 * | 11/2001 | Phillips et al. | 514/44 |

FOREIGN PATENT DOCUMENTS

| WO | WO 96/23508 | 8/1996 |
|---|---|---|
| WO | WO 97/14440 | 4/1997 |
| WO | WO-99/011813 | 3/1999 |
| WO | WO-00/008141 | 2/2000 |
| WO | WO 00/09073 A2 | 2/2000 |
| WO | WO 01/44465 A2 | 6/2001 |

OTHER PUBLICATIONS

Bates, P.J., et al. "Antiproliferative Activity of G-rich Oligonucleotides Correlates with Protein Binding", *The Journal of Biological Chemistry*, vol. 274, No. 37, pp. 26369-26377, Sep. 10, 1999.
Boutorin, A.S., et al. "Synthesis of Alkylating Oligonucleotide Derivatives Containing Cholesterol or Phenazinium Residues at Their 3'-terminus and Their Interaction with DNA Within Mammalian Cells", *FEBS Letters*, vol. 254, No. 1,2, pp. 129-132, Aug. 28, 1989.
Corrias, M.V., et al., "Bioavailability of Antisense Oligonucleotides in Neuroblastoma Cells: Comparison of Efficacy Among Different Types of Molecules", *Journal of Neuro-Oncology*, vol. 31, pp. 171-180, 1997.
EPA, W.R., et al., "Enhanced Downregulation of the p75 Nerve Growth Factor Receptor by Cholesteryl and Bis-Cholesteryl Antisense Oligonucleotides", *Antisense & Nucleic Acid Drug Development*, vol. 8, pp. 489-498, 1998.
Green, S.K., et al., "Adhesion-dependent Multicellular Drug Resistance", *Anti Cancer Drug Design*, vol. 14, pp. 153-168, 1999.
Hackett, A.J., et al., "Two Syngeneic Cell Lines from Human Breast Tissue: The Aneuploid Mammary Epithelial (Hs578T) and the Diploid Myoepithelial (Hs578Bst) Cell Lines", *J. Natl. Cancer Inst.*, vol. 58, No. 6, pp. 1795-1806, Jun. 1977.
Herrera-Gayol, A., et al., "Effects of Hylauronan on the Invasive Properties of Human Breast Cancer Cells in Vitro", *Int. J. Emp. Path.*, vol. 82, pp. 193-200, 2001.
Koopman, G., et al., "Annexin V for Flow Cytometric Detection of Phosphatidylserine Expression on B Cells Undergoing Apoptosis", *Blood*, vol. 84, No. 5, pp. 1415-1420, Sep. 1, 1994.
Krawczyk, C.M., et al., "Protective Specific Immunity Induced by Cyclophosphamide Plus Tumor Necrosis Factor α Combination Treatment of EL4-limphoma-bearing C57BL/6 Mice", *Cancer Immunol Immunother*, vol. 40, pp. 347-357, 1995.
Letsinger, R.L., et al., "Cholesteryl-conjugated Oligonucleotides: Synthesis, Properties, and Activity as Inhibitors of Replication of Human Immunodeficiency Virus in Cell Culture", *Proc. Natl. Acad. Sci. USA*, vol. 86, pp. 6553-6556, Sep. 1989.
Martin, S.J., et al., "Early Redistribution of Plasma Membrane Phosphatidylserine Is a General Feature of Apoptosis Regardless of the Initiating Stimulus: Inhibition by Overexpression of Bcl-2 and Abl", *J. Exp. Med.*, vol. 182, pp. 1545-1556, Nov. 1995.
O'Brian, M.A., et al., "Poly (ADP-Ribose) Polymerase Cleavage Monitored In Situ in Apoptotic Cells", *Biotechniques*, vol. 30, pp. 886-891, Apr. 2001.
Price, J.E., et al., "Tumorigenicity and Metastasis of Human Breast Carcinoma Cell Lines in Nude Mice", *Cancer Research*, vol. 50, pp. 717-721, Feb. 1, 1990.
Peiper, M., et al., "Human Pancreatic Cancer Cells (MPANC-96) Recognized by Autologous Tumor-Infiltrating Lymphocytes After in Vitro as Well as in Vivo Tumor Expansion", *Int. J. Cancer*, vol. 71, pp. 993-999, 1997.

(Continued)

*Primary Examiner*—Sheela J Huff
(74) *Attorney, Agent, or Firm*—Kilpatrick Stockton LLP

(57) ABSTRACT

The present invention provides a composition comprising a 5'-OH, 3'-TEG cholesteryl synthetic sequence wherein the sequence is SEQ ID NO:5, SEQ ID NO:6, SEQ ID NO:7, SEQ ID NO:8. The present invention provides methods of using this composition for induction of response in a cell, including but not limited to inhibition of cellular proliferation, induction of cell cycle arrest, induction of caspase activation, cleavage of poly(ADP-ribose) polymerase, induction of apoptosis or modulation of extracellular matrix-cell interactions, or combinations thereof, in cancer cells or synovial cells, and methods of using this composition for treating disease.

29 Claims, 5 Drawing Sheets

OTHER PUBLICATIONS

Radisky, D., et al., "Tumors are Unique Organs Defined by Abnormal Signaling and Context", *Cancer Biology*, vol. 11, pp. 87-95, 2001.

Saxon, M., et al., "Stimulation of Calcium Influx in HL60 Cells by Cholesteryl-Modified Homopolymer Oligodeoxynucleotides", *Antisense Research and Development*, vol. 2, pp. 243-250, 1992.

Scaggiante, B., et al., "Human Cancer Cell Lines Growth Inhibition by $GT^n$ Oligodeoxyribonucleotides Recognizing Single-Stranded DNA-binding Proteins", *Eur. J. Biochem.*, vol. 252, pp. 201-215, 1998.

Stein, C.A., et al., "Mode of Action of 5'-Linked Cholesteryl Phosphorothioate Oligodeoxynucleotides in Inhibiting Syncytia Formation and Infection by HIV-1 and HIV-2 in Vitro", *Biochemistry*, vol. 30., pp. 2439-2444, 1991.

Susin, S.A., et al., "The Central Executioner of Apoptosis: Multiple Connections Between Protease Activation and Mitochondria in Fas/APO-1/CD95- and Ceramide-Induced Apoptosis", *J. Exp. Med.*, vol. 186, No. 1, pp. 25-37, Jul. 7, 1997.

Takeo, T., et al., "New Xenografts of Human Megakaryoblastic Cell Line (MEG-01) for Evaluating Anti-Tumor Agents", *Leukemia*, vol. 7, No. 8, pp. 1268-1274, Aug. 1993.

Thompson, E.W., et al., "Association of Increased Basement Membrane Invasiveness with Absence of Estrogen Receptor and Expression of Vimentin in Human Breast Cancer Cell Lines", *Journal of Cellular Physiology*, vol. 150, pp. 534-544, 1992.

Thornberry, N.A., et al., "A Combinatorial Approach Defines Specificities of Members of the Caspase Family and Granzyme B", *Journal of Biological Chemistry*, vol. 272, No. 29, pp. 17907-17911, Jul. 18, 1997.

Vlassov, V.V., et al., "Transport of Oligonucleotides Across Natural and Model Membranes", *Biochimica et Biophysica Acta*, vol. 1197, pp. 95-108, 1994.

Wagner, W.R., "Gene Inhibition Using Antisense Oligodeoxynucleotides", *Nature*, vol. 372, pp. 333-335, Nov. 24, 1994.

Weaver, V.M., et al., "Reversion of the Malignant Phenotype of Human Breast Cells in Three-Dimensional Culture and In Vivo by Integrin Blocking Antibodies", *Journal of Cell Biology*, vol. 137, No. 1, pp. 231-245, Apr. 7, 1997.

Wyllie, A.H., et al., "Cell Death: The Significance of Apoptosis", *International Review of Cytology*, vol. 68, pp. 251-307, 1980.

\* cited by examiner

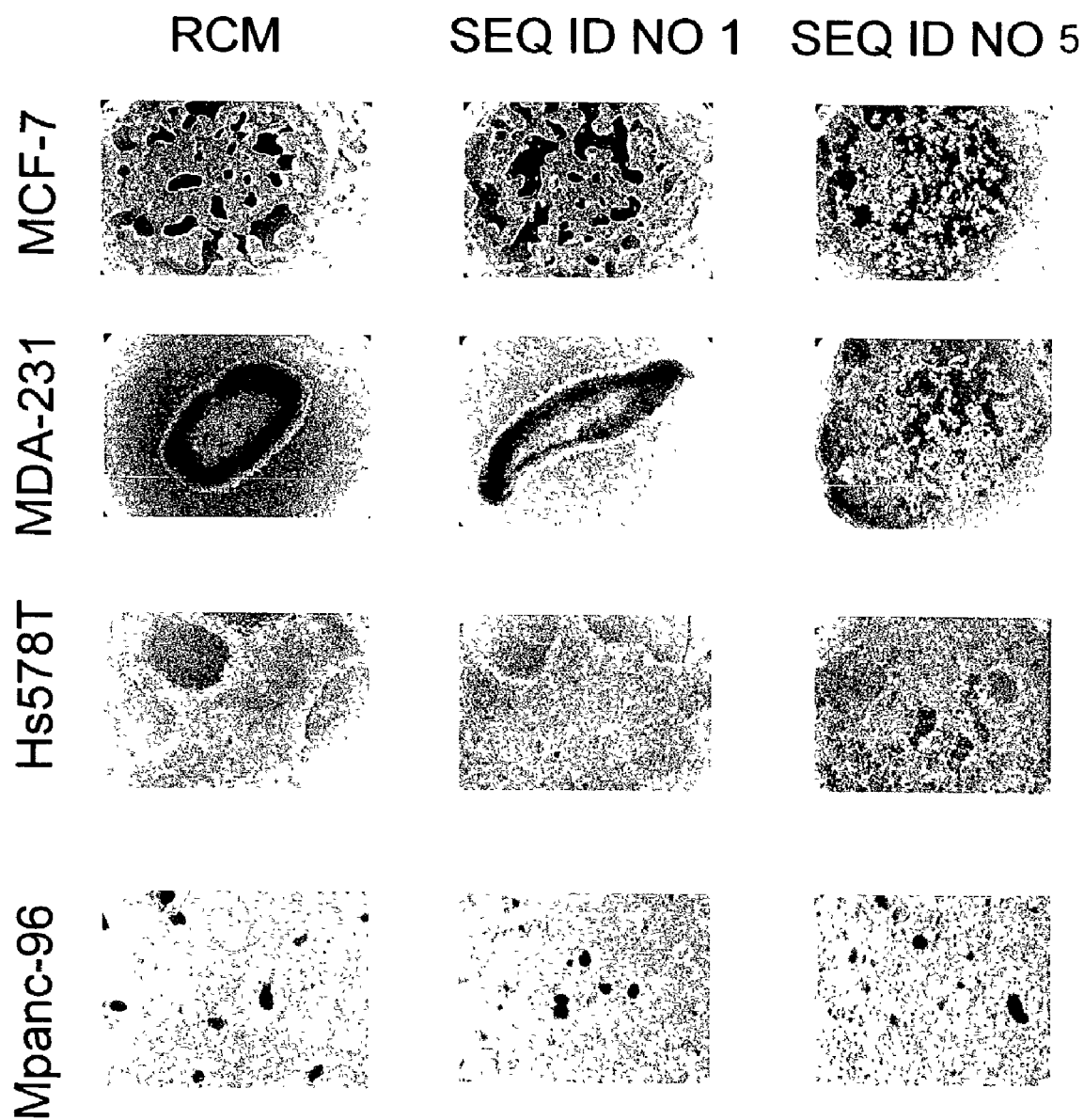
Figure 1: Growth on Matrigel® with pre-incubation. Analysis at day 3.

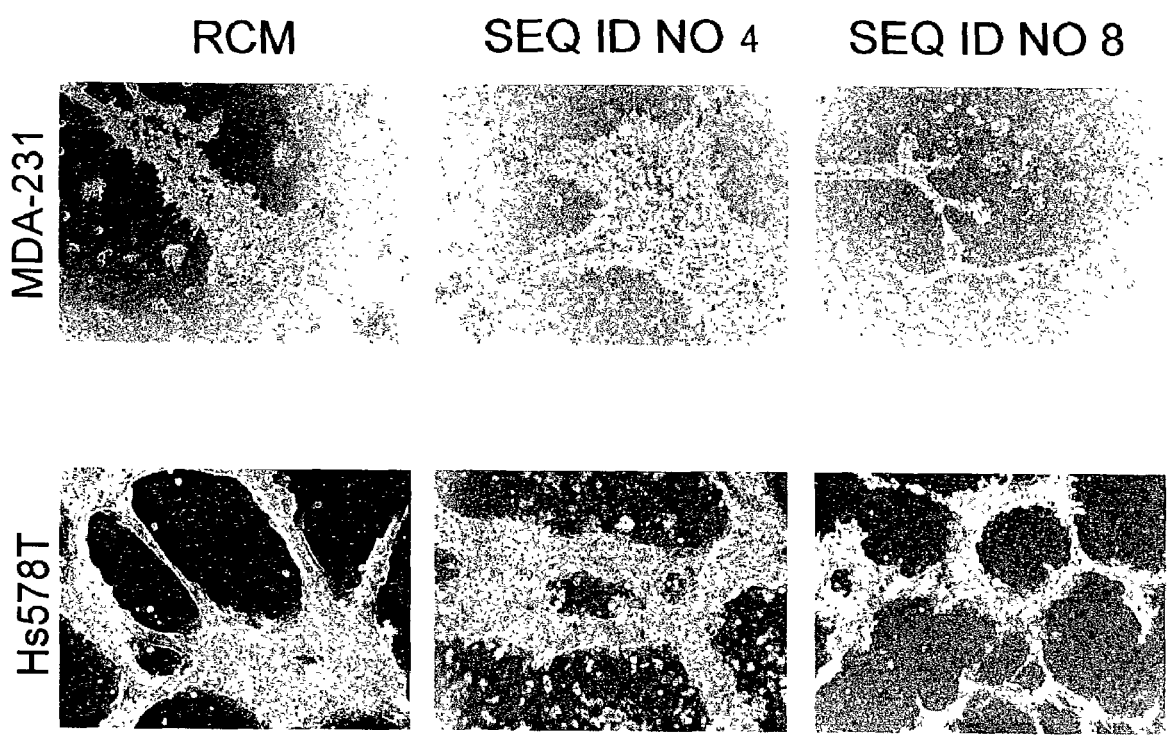
Figure 2: Growth on Matrigel® with pre-incubation. Analysis at day 3.

Figure 3: MCF-7 cell line: growth on Matrigel®, treatments added after 48 hrs of culture. Analysis at days 19-20
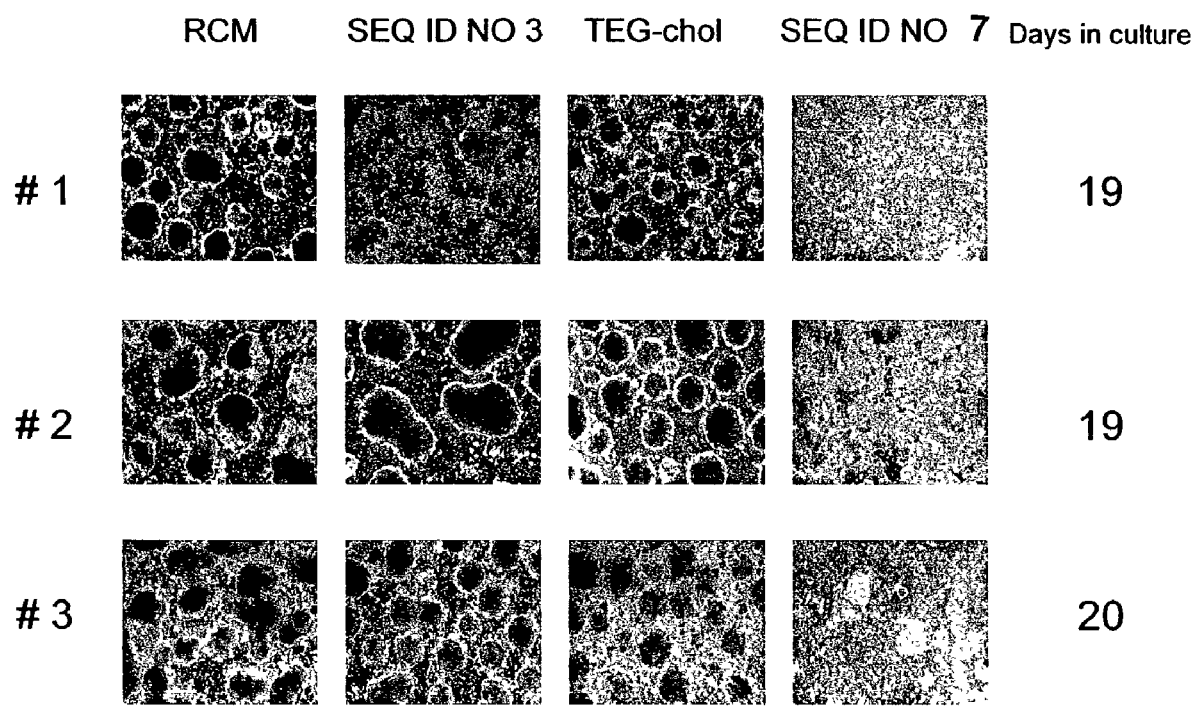

Figure 4: MDA-231 cell line: growth on Matrigel®, treatments added after 48hrs of culture. Analysis at days 17-21
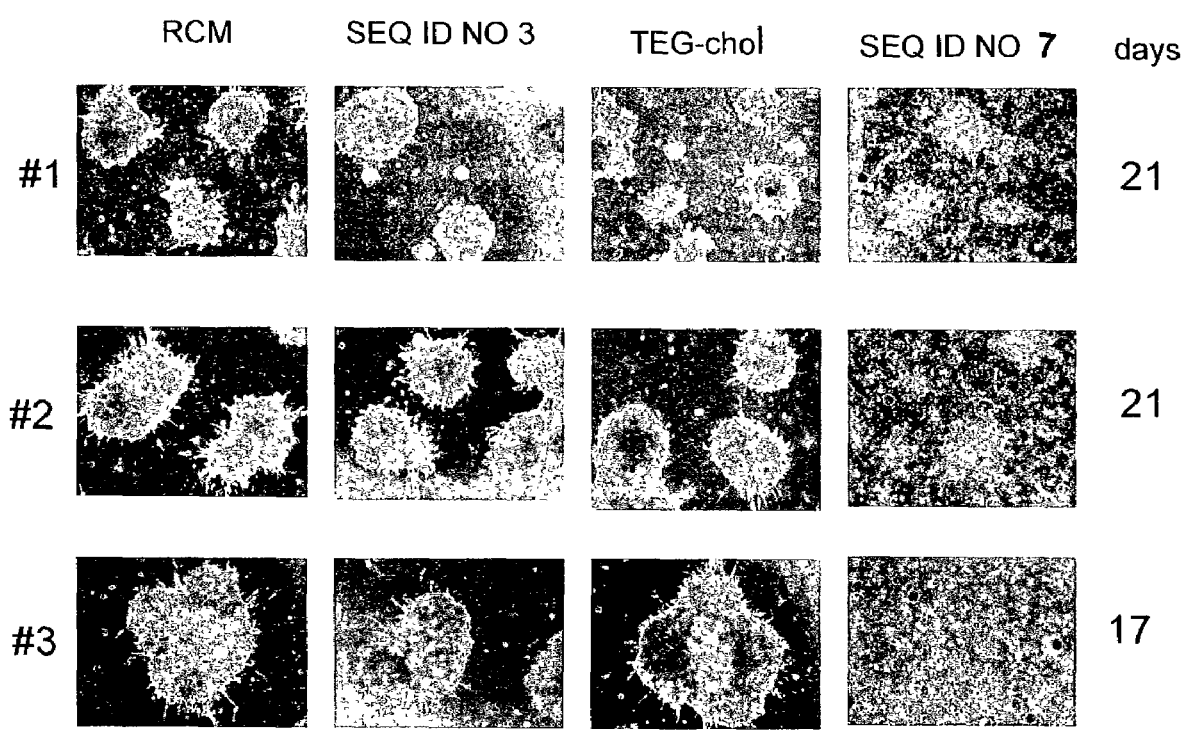

Figure 5: Changes in cell cycle progression when Hs578T spheroids were in culture for 3 days in different treatments.
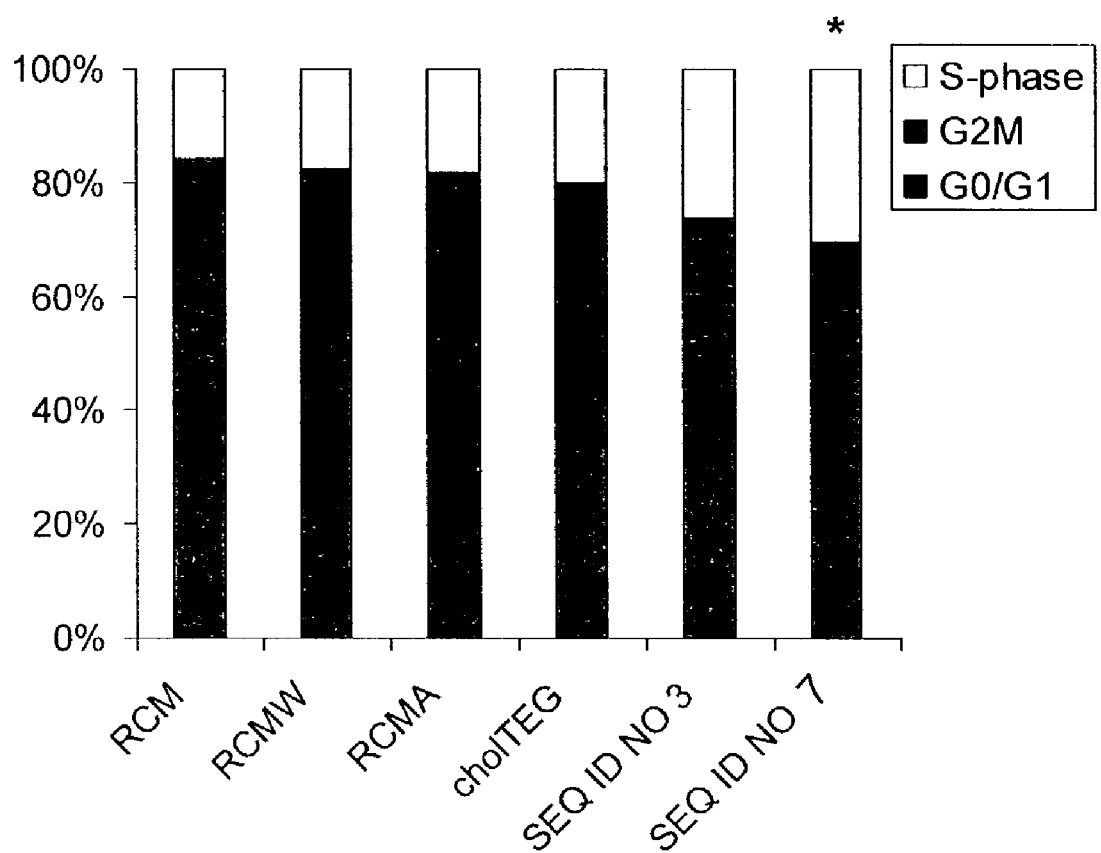
\* $p < 0.05$

US 7,635,686 B2

THERAPEUTICALLY USEFUL TRIETHYLENEGLYCOL CHOLESTERYL OLIGONUCLEOTIDES

PRIOR RELATED APPLICATIONS

The present application claims benefit to U.S. Provisional Patent Application Ser. No. 60/326,884, filed Oct. 3, 2001.

FIELD OF THE INVENTION

The present invention relates to cholesteryl-conjugated oligonucleotide compositions and their use for the inhibition of cellular proliferation, induction of apoptosis, modification of cell cycle progression and modulation of extracellular matrix-cell interaction.

BACKGROUND OF THE INVENTION

Proliferation is the culmination of a cell's progression through the cell cycle resulting in the division of one cell into two cells. The five major phases of the cell cycle are $G_0$, $G_1$, S, $G_2$, and M. During the $G_0$, phase, cells are quiescent. Most cells in the body, at one time, are in this stage. During the $G_1$ phase, cells, responding to signals to divide, produce the RNA and the proteins necessary for DNA synthesis. During the S-phase (SE, early S-phase; SM, middle S-phase; and SL, late S-phase) the cells replicate their DNA. During the $G_2$ phase, proteins are elaborated in preparation for cell division. During the mitotic (M) phase, the cell divides into two daughter cells. Alterations in cell cycle progression occur in all cancers and may result from over-expression of genes, mutation of regulatory genes, or abrogation of DNA damage checkpoints (Hochhauser D., Anti-Cancer Chemotherapeutic Agents, 8:903, 1997).

Apoptosis or programmed cell death is the physiological process for the killing and removal of unwanted cells, and a mechanism whereby chemotherapeutic agents kill cancer cells. Apoptosis is characterized by distinctive morphological changes within cells that include condensation of nuclear chromatin, cell shrinkage, nuclear disintegration, plasma membrane blebbing, and the formation of membrane-bound apoptotic bodies (Wyllie et al., Int. Rev. Cytol., 68: 251, 1980). The translocation of phosphatidylserine from the inner face of the plasma membrane to the outer face coincides with chromatin condensation and is regarded as a cellular hallmark of apoptosis (Koopman, G. et al., Blood, 84:1415, 1994). The mechanism of apoptosis is known to be mediated by the activation of a family of cysteine proteases, known as caspases.

Caspases recognize three major peptide sequences as substrates (Thornberry et al., J. Biol. Chem. 272:17907, 1997): (i) Tyr-Val-Ala-Asp (YVAD, caspase-1, -4), (ii) Asp-Glu-Val-Asp (DEVD, caspase-2, -3 and -7), and, (iii) Ile-(Leu)-Glu-X-Asp (I(L)EXD; caspase-8 and -10). Sequence recognition in a protein target results in a limited and specific proteolysis of the target, such as activation of caspase-7 by caspase-3, degradation of structural protein targets including, but not limited to, lamins, or activation of enzymes including, but not limited to, poly(ADP-ribose) polymerase. Caspase-3 was reported to be cleaved into its catalytically active subunits (17 and 13 kDa) following pro-apoptotic signals, leading to apoptosis (Susin et al., J. Exp. Med. 186:25, 1997).

During apoptosis, the activation of caspases results in proteolytic cleavage of numerous substrates. Poly(ADP-ribose) polymerase (PARP), a nuclear enzyme involved in DNA repair, is a well-known substrate for caspase-3 cleavage during apoptosis. Its cleavage is considered to be a hallmark of apoptosis (O'Brien et al., Biotechniques 30:886, 2001).

The extracellular matrix (ECM) impacts behavior of normal and tumor cells (Radisky et al., Seminars Cancer Biol., 11:87, 2001). Therefore, the interaction between tumor cells and the ECM components, when tumor cells are plated on the ECM, will activate signal transduction events mimicking several biopathological characteristics of tumors in vivo, such as modulation of cell-cell contacts (Weaver et al., J. Cell Biol., 137:231, 1997).

Synthetic oligonucleotides are polyanionic sequences that are internalized in cells (Vlassov et al., Biochim. Biophys. Acta, 11197:95, 1994). Synthetic oligonucleotides were reported that bind selectively to nucleic acids (Wagner, R., Nature, 372:333, 1994), to specific cellular proteins (Bates et al., J. Biol. Chem., 274:26369, 1999) and to specific nuclear proteins (Scaggiante et al., Eur. J. Biochem, 252:207, 1998) in order to inhibit proliferation of cancer cells.

Synthesis and physical properties of oligonucleotides with a cholesteryl moiety have been described. The attachment of a cholesteryl moiety to the 3'-end of antisense oligonucleotides enhances their activities (Letsinger et al., Proc. Natl. Acad. Sci. USA, 86:6553, 1989; Boutorin et al., FEBS Letter, 254:129, 1989; Corrias et al., J. Neurooncol. 31:171, 1997; U.S. Pat. No. 4,958,013; WO Patent No. 9714440). The attachment of a cholesteryl moiety to the 3'-end enhances the uptake of antisense molecules by cells (Corrias et al., J. Neurooncol. 31:171, 1997), and increases antisense vascular retention in vivo (Fleser et al., Circulation 92:1296, 1995). Internucleoside cholesteryl side chains linked to phosphorous via phosphoramidate bonds have been described as a modification to increase the activity of antisense molecules (U.S. Pat. No. 4,958,013). Homopolymers of 15 cytidine or thymidine residues with a cholesteryl moiety at the 5'-end were found to modulate cytosolic $Ca^{2+}$ levels in pro-myelocytic leukemia cells, while heteropolymeric sequences with a cholesteryl moiety at the 5'-end or cholesteryl-modified phosphorothioate sequences were inactive (Saxon et al., Antisense Res. Dev. 2:243, 1992). Heteropolymers consisting of 15 phosphorothioate deoxynucleotides with alternating cytosine and adenosine residues, or homopolymers with 15 cytosine or thymidine residues, were shown to be potent inhibitors of methotrexate transport when a cholesteryl group was linked to the 5'-end (Henderon et al., Nucl. Acids Res. 25:3726, 1995). The covalent modification of a 10 base homocytidine phosphorothioate oligonucleotide with a cholesteryl moiety at the 5'-end blocked the formation of syncitia in T lymphocytes infected with HIV-1 or HIV-2 through inhibition of HIV reverse transcriptase (Stein et al., Biochemistry 5:2439, 1991).

The attachment of a cholesteryl moiety to oligonucleotides has minimal effects on the growth of cancer cells (Henderon et al., Nucl. Acids Res. 25:3726, 1995). Typical features of apoptotic cell death were not observed in cancer cell lines treated with 3'-end cholesteryl oligonucleotides (Corrias et al., J. Neurooncol. 31:171, 1997).

Most anti-cancer therapies, whether directed to inhibition of proliferation, induction of cell cycle arrest, induction of apoptosis, stimulation of the immune system or modulation of extracellular matrix-cell interaction have proven to be less than adequate for clinical applications. Many of these therapies are inefficient or toxic, have significant adverse effects, result in development of drug resistance or immunosensitization, and are debilitating for the recipient Therefore, there is a continuing need for novel compositions and methods that induce cell cycle arrest in cancer cells, that induce apoptosis in cancer cells, and that modulate extracellular matrix-cell interactions.

SUMMARY OF THE INVENTION

The present invention fulfills this need by providing a composition, wherein a triethyleneglycol (TEG) cholesteryl moiety is attached to the 3' end of synthetic oligonucleotide sequences SEQ ID NO:1 (5' OH-GGGTGG-OH 3'), SEQ ID NO:2 (5' OH-GGGAGG-OH 3'), SEQ ID NO:3 (5' OH-CCACCC-OH 3'), or SEQ ID NO:4 (5' OH-GTG-OH 3'), resulting in corresponding 5'-OH, 3'TEG cholesteryl novel synthetic oligonucleotide sequences SEQ ID NO:5 (5' OH-GGGTGG(TEG-cholesteryl) 3'), SEQ ID NO:6 (5' OH-GGAGG(TEG-cholesteryl) 3'), SEQ ID NO:7 (5' OH-CCACCC(TEG-cholesteryl) 3'), or SEQ ID NO:8 (5'OH-GTG(TEG-cholesteryl) 3'). The present invention also provides methods for using these novel synthetic oligonucleotide sequences by combining them with an acceptable carrier to make a composition, and administering the composition in vitro or in vivo. The composition is administered to an animal, including a human, in order to induce a response in a cell. Such responses include, but are not limited to, inhibition of cellular proliferation, induction of cell cycle arrest, induction of apoptosis, activation of caspase, cleavage of poly (ADP-ribose) polymerase, or modulation of extracellular matrix-cell interactions, or a combination thereof. A preferred cell for induction of the response is a cancer cell or a synovial cell. Any disease or condition characterized by undesired cellular proliferation may be treated with the compositions of the present invention. Such diseases or conditions characterized by undesired cellular proliferation include, but are not limited to, autoimmune disease, inflammation, lymphoproliferative disease, arthritis and cancer.

One or more novel sequences of the present invention may be combined with an acceptable carrier and administered as a composition in vitro in cells or tissues in culture, or in vivo to an animal or human. Further, the compositions of the present invention may be administered together with one or more therapeutic agent. Such administration of the compositions of the present invention may occur before, during or after administration of one or more therapeutic agents known to one of ordinary skill in the medical or veterinary arts. Any therapeutic agent known to one of ordinary skill in the medical or veterinary arts, and employed to treat diseases, may be used in combination with these novel sequences. Such combinations may permit use of lower dosages of therapeutic agents, thereby decreasing unwanted side effects.

Administration of a composition comprising an effective amount of one or more of the sequences of the present invention to an animal or human is a therapeutic treatment that prevents, treats or eliminates a disease or condition characterized by undesired cellular proliferation. Such diseases and conditions are known to one of skill in the medical or veterinary arts and include, but are not limited to, cancer, inflammation, arthritis, lymphoproliferative disorders, asthma and restenosis of arteries following angioplasty. Cancers include, but are not limited to, squamous cell carcinoma, fibrosarcoma, sarcoid carcinoma, melanoma, breast cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma, and metastases derived therefrom.

Methods and routes of administration of therapeutic agents to animals and humans are known to one of ordinary skill in the art and may be employed to administer compositions comprising the sequences of the present invention and a pharmaceutically acceptable carrier.

The unexpected and surprising ability of the covalent attachment of a cholesteryl-TEG phosphoramidite moiety to the 3'-oxygen of functionally inert 3'-OH oligonucleotides to inhibit the proliferation of cancer cells and synovial cells, to induce apoptosis in cancer cells and synovial cells, to modulate extracellular matrix-cell interactions in cancer cells, and to modify cell cycle progression of cancer cells addresses long-felt and unfulfilled needs in the medical arts and provides an important benefit for animals, including humans.

Accordingly, it is an object of the present invention to provide a novel composition comprising a 5'-OH, 3'-TEG cholesteryl synthetic sequence.

Another object of the present invention is to provide a composition and method effective to treat a disease in an animal, including a human.

Still another object of the present invention is to provide a composition and method effective to treat a disease or a condition characterized by undesired cellular proliferation.

Yet another object of the present invention is to provide a composition and method effective to treat cancer.

Yet another object of the present invention is to provide a composition and method effective to treat arthritis.

Still another object of the present invention is to provide a composition and method that induces a response in cells, including but not limited to inhibition of cellular proliferation, induction of cell cycle arrest, induction of caspase activation, cleavage of poly(ADP-ribose) polymerase, induction of apoptosis or modulation of extracellular matrix-cell interactions, or combinations thereof.

Still another object of the present invention is to provide a composition and method that induces a response, including but not limited to inhibition of cellular proliferation, induction of cell cycle arrest, induction of caspase activation, cleavage of poly(ADP-ribose) polymerase, induction of apoptosis or modulation of extracellular matrix-cell interactions, or combinations thereof, in cancer or synovial cells, including drug-resistant cancer or synovial cells.

Another object of the present invention is to provide a composition and method that induces apoptosis in cells independent of BCR-ABL (a fusion of the BCR gene on chromosome 22 and ABL gene on chromosome 9).

Yet another object of the present invention is to provide a composition and method that induces apoptosis in cells independent of p53 mutation.

Another object of the present invention is to provide a composition that is simple to prepare.

Still another object of the present invention is to provide a composition that is minimally toxic to the recipient.

These and other objects, features and advantages of the present invention will become apparent after a review of the following detailed description of the disclosed non-limiting embodiment and the appended claims.

BRIEF DESCRIPTION OF THE DRAWINGS

FIG. 1. Photographs of growth of MCF-7, MDA-MB-231 (MDA-231), Hs578T and Mpanc-96 cells on MATRIGEL® following pre-incubation with regular culture medium (RCM) alone, or with added SEQ ID NO:1 or SEQ ID NO:5.

FIG. 2. Photographs of growth of human breast cancer cells on MATRIGEL® following pre-incubation with regular culture medium (RCM) alone, with added SEQ ID NO:4 or SEQ ID NO:8.

FIG. 3. Photographs of MCF-7 cells that were allowed to grow on MATRIGEL®-coated wells for 48 hrs. Then, the resulting 3-dimensional cell structures were exposed to regular culture medium (RCM) alone, or with added cholesteryl-TEG phosphoramidite, to SEQ ID NO:3 or to SEQ ID NO:7.

FIG. 4. Photographs of MDA-231 cells that were allowed to grow on MATRIGEL®-coated wells for 48 hrs. Then, the resulting three-dimensional cell structures were exposed to regular culture medium (RCM) alone, with added cholesteryl-TEG phosphoramidite, SEQ ID NO:3 or SEQ ID NO:7.

FIG. 5. Photographs of Hs578T cells that were grown as spheroids and exposed for 3 days to regular culture medium (RCM) with or without addition of cholesteryl-TEG phosphoramidite (chol-TEG), SEQ ID NO:3, SEQ ID NO:7, or to the corresponding controls (RCM plus water (RCMW) and RCM plus acetonitrile (RCMA).

DETAILED DESCRIPTION OF THE INVENTION

The present invention provides novel compositions comprising 5'-OH, 3'-TEG cholesteryl synthetic sequences, As used herein, the word "sequence" refers to a 3'-OH, 5'-OH synthetic oligonucleotide comprising SEQ ID NO:1 (5' OH-GGGTGG-OH 3'), SEQ ID NO:2 (5' OH-GGGAGG-OH 3'), SEQ ID NO:3 (5' OH-CCACCC-OH 3'), or SEQ ID NO:4 (5' OH-GTG-OH 3'), or to a 5'-OH, 3'-TEG cholesteryl synthetic oligonucleotide comprising SEQ ID NO:5 (5' OH-GGGTGG(TEG-cholesteryl) 3'), SEQ ID NO:6 (5' OH-GGGAGG(TEG-cholesteryl) 3'), SEQ ID NO:7 (5' OH-CCACCC(TEG-cholesteryl) 3'), or SEQ ID NO:8 (5'OH-GTG(TEG-cholesteryl) 3').

As used herein, the terms "3'-TEG cholesteryl oligonucleotide" and "3'-TEG cholesteryl synthetic oligonucleotide" refer to a 3'-triethyleneglycol cholesteryl-modified oligonucleotide, a 5'-OH oligonucleotide with a TEG cholesteryl moiety attached at the 3' end. For illustrative purposes, the chemical structure of SEQ ID NO:7, an example of a 5'-OH, 3'-TEG cholesteryl synthetic oligonucleotide, is shown below.

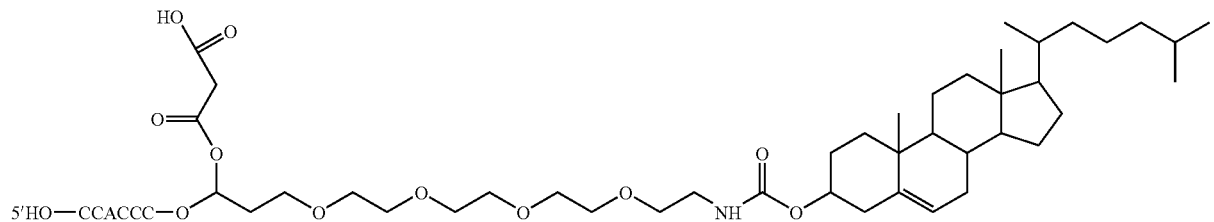

wherein the sequence is SEQ ID NO:5 (5' OH-GGGTGG(TEG-cholesteryl) 3'), SEQ ID NO:6 (5' OH-GGGAGG(TEG-cholesteryl) 3'), SEQ ID NO:7 (5' OH-CCACCC(TEG-cholesteryl) 3') or SEQ ID NO:8 (5' OH-GTG(TEG-cholesteryl) 3').

The present invention also provides methods for using these novel compositions. The compositions of the present invention are useful for inducing a response in a cell when administrated to animals or humans, in an amount effective to induce a response in the cell. These responses include but are not limited to inhibition of cellular proliferation, cell cycle arrest, induction of apoptosis, activation of caspase, cleavage of poly(ADP-ribose) polymerase in the cell, or modulation of extracellular matrix-cell interactions, or a combination thereof. In one embodiment, the animal or human has cancer or arthritis. In a preferred embodiment, the cells are cancer cells. In another preferred embodiment, the cells are synovial cells.

The compositions of the present invention may be used to treat diseases or conditions characterized by undesired cellular proliferation. In one embodiment, a composition of the present invention is administered to an animal or human having cancer in an amount effective to treat the cancer in the animal or the human.

In another embodiment, the composition of the present is administered to an animal or human having arthritis in an amount effective to treat arthritis in the animal or the human.

The unexpected and surprising ability of the 3'-TEG cholesteryl oligonucleotides to inhibit proliferation, induce cell cycle arrest, induce apoptosis, activate caspases, or modulate extracellular matrix-cell interactions in cells, or induce a combination these responses in cells fulfills a long-felt unfulfilled need in the medical arts and provides an important benefit for animals and humans.

As used herein, the word "response" refers to induction of a response, including but not limited to inhibition of cellular proliferation, induction of cell cycle arrest, activation of caspases, cleavage of poly(ADP-ribose) polymerase, induction of apoptosis in cells or modulation of extracellular matrix-cell interactions, or a combination thereof.

As used herein, the phrase "effective in responsive cells" refers to the ability of a sequence to induce a response, including but not limited to ability of the sequence to inhibit cellular proliferation, induce cell cycle arrest, induce activation of caspases, induce cleavage of poly(ADP-ribose) polymerase, induce apoptosis in cells or modulate extracellular matrix-cell interactions, or a combination thereof.

As used herein, the phrases "therapeutic treatment", "effective amount" and "amount effective to" refer to an amount of a sequence effective to induce a response, including but not limited to inhibition of cellular proliferation, cell cycle arrest, activate caspases, cleave poly(ADP-ribose) polymerase, induce apoptosis in cells, modulate extracellular matrix-cell interactions, or a combination thereof.

As used herein, the word "disease" relates to a condition wherein bodily health is impaired.

As used herein, the phrase "therapeutic agent" is any agent, including radiation, approved by a regulatory agency of a country or a state government or listed in the U.S. Pharmacopoeia or other generally recognized pharmacopoeia for use to treat a disease in an animal, including a human.

As used herein, the phrase "chemotherapeutic" is any agent approved by a regulatory agency of a country or a state government, or listed in the U.S. Pharmacopoeia or other generally recognized pharmacopoeia to treat disease in an animal, including a human.

As used herein, the phrase "anti-arthritic" is any agent approved by a regulatory agency of a country or a state government or listed in the U.S. Pharmacopoeia or other generally recognized pharmacopoeia for use in the treatment of arthritis in an animal, including a human.

As used herein, the word "antineoplastic" refers to preventing the development, progression, proliferation or spread of cancer cells.

Administration of an effective amount of a composition of the present invention to an animal, or human, is a therapeutic treatment that induces a response, prevents, treats, or eliminates a disease, or a combination thereof. The response includes but is not limited to, inhibition of cellular proliferation, cell cycle arrest, activation of caspases, cleavage of poly(ADP-ribose) polymerase, induction of apoptosis in cells, modulation of extracellular matrix-cell interactions, or a combination thereof. The disease includes, but is not limited to, cancer, arthritis, lymphoproliferative disorders and inflammation. Cancers include, but are not limited to, squamous cell carcinoma, fibrosarcoma, hemangiosarcoma, lymphangiosarcoma, rhabdomyosarcoma, leiomyosarcoma, liposarcoma, chondrosarcoma, sarcoid carcinoma, melanoma, breast cancer, lung cancer, colorectal cancer, renal cancer, osteosarcoma, cutaneous melanoma, basal cell carcinoma, pancreatic cancer, bladder cancer, brain cancer, ovarian cancer, prostate cancer, leukemia, lymphoma, myeloma and metastases derived therefrom. Forms of arthritis include, but are not limited to, juvenile arthritis, osteoarthritis and rheumatoid arthritis.

The therapeutic effectiveness of a sequence may be increased by methods including, but not limited to, chemically modifying the base, sugar or phosphate backbone, chemically supplementing or biotechnologically amplifying the sequences using bacterial plasmids containing the appropriate sequences, complexing the sequences to biological or chemical carriers, or coupling the sequences to tissue-type or cell-type directed ligands or antibodies.

Compositions comprising one or more sequences and a pharmaceutically acceptable carrier are prepared by uniformly and intimately bringing into association the sequence and the pharmaceutically acceptable carrier. The terms "pharmaceutically acceptable carrier" or "pharmaceutically acceptable vehicle" are used herein to mean, without limitation, any liquid, solid or semi-solid, including, but not limited to, water or saline, a gel, cream, salve, solvent, diluent, fluid ointment base, ointment, paste, implant, liposome, micelle, giant micelle, and the like, which is suitable for use in contact with living animal or human tissue without causing adverse physiological responses, and which does not interact with the other components of the composition in a deleterious manner. Other pharmaceutically acceptable carriers or vehicles known to one of skill in the art may be employed to make compositions for delivering the oligonucleotide sequences of the present invention. Liquid carriers are aqueous carriers, non-aqueous carriers or both and include, but are not limited to, aqueous suspensions, dimethyl sulfoxide, ethanol, oil emulsions, water in oil emulsions, water-in-oil-in-water emulsions, site-specific emulsions, long-residence emulsions, sticky-emulsions, microemulsions and nanoemulsions. Solid carriers are biological carriers, chemical carriers or both and include, but are not limited to, viral vector systems, particles, microparticles, nanoparticles, microspheres, nanospheres, minipumps, bacterial cell wall extracts and biodegradable or non-biodegradable natural or synthetic polymers that allow for sustained release of the sequences. Emulsions, minipumps and polymers can be implanted in the vicinity of where delivery is required. Methods used to complex a sequence(s) to a solid carrier include, but are not limited to, direct adsorption to the surface of the solid carrier, covalent coupling to the surface of the solid carrier, either directly or via a linking moiety, and covalent coupling or electrostatic coupling to the polymer used to make the solid carrier. Optionally, a sequence(s) can be stabilized by the addition of non-ionic or ionic polymers such as polyoxyethylenesorbitan monooleates (Tweens), hyaluronic acid or aluminum hydroxide. Other carriers known to one of ordinary skill in the art may be employed.

Preferred aqueous carriers include, but are not limited to, water, saline and pharmaceutically acceptable buffers. Preferred non-aqueous carriers include, but are not limited to, a mineral oil or a neutral oil including, but not limited to, a diglyceride, a triglyceride, a phospholipid, a lipid, an oil and mixtures thereof, wherein the oil contains an appropriate mix of polyunsaturated and saturated fatty acids. Examples include, but are not limited to, soybean oil, canola oil, palm oil, olive oil and myglyol, wherein the fatty acids can be saturated or unsaturated. Optionally, excipients may be included regardless of the pharmaceutically acceptable carrier used to present the sequence to the responding cells. These excipients include, but are not limited to, anti-oxidants, buffers, and bacteriostats, and may include suspending agents and thickening agents.

The sequences of the present invention may be combined with pharmaceutically acceptable carriers and administered as compositions in vitro to cells or tissues in culture, or in vivo to animals or humans. Forms of administration include, but are not limited to, injections, solutions, creams, gels, implants, pumps, ointments, emulsions, suspensions, microspheres, particles, microparticles, nanoparticles, liposomes, pastes, patches, tablets, transdermal delivery devices, sprays, aerosols, or other means familiar to one of ordinary skill in the art. Such pharmaceutically acceptable carriers are commonly known to one of ordinary skill in the art. Pharmaceutical formulations of the present invention can be prepared by procedures known in the art using well known and readily available ingredients. For example, the compounds can be formulated with common excipients, diluents, or carriers, and formed into tablets, capsules, suspensions, powders, and the like. Examples of excipients, diluents, and carriers that are suitable for such formulations include the following: fillers and extenders (e.g., starch, sugars, mannitol, and silicic derivatives); binding agents (e.g., carboxymethyl cellulose and other cellulose derivatives, alginates, gelatin, and polyvinylpyrrolidone); moisturizing agents (e.g., glycerol); disintegrating agents (e.g., calcium carbonate and sodium bicarbonate); agents for retarding dissolution (e.g., paraffin); resorption accelerators (e.g., quaternary ammonium compounds); surface active agents (e.g., cetyl alcohol, glycerol monostearate); adsorptive carriers (e.g., kaolin and bentonite); emulsifiers; preservatives; sweeteners; stabilizers; coloring agents; perfuming agents; flavoring agents; lubricants (e.g., talc, calcium and magnesium stearate); solid polyethyl glycols; and mixtures thereof.

The formulations can be so constituted that they release the active ingredient only or preferably in a particular location, possibly over a period of time. Such combinations provide yet a further mechanism for controlling release kinetics. The coatings, envelopes, and protective matrices may be made, for example, from polymeric substances or waxes.

One or more sequences may be administered alone, or in combination with other therapeutic modalities including, but not limited to, chemotherapeutic agents, anti-arthritic agents, immunotherapeutic agents, antimicrobial agents, or antiviral agents, or in combination with radiation therapy, or any combination thereof. Chemotherapeutic agents include, but are not limited to, anti-metabolites, DNA damaging, microtubule destabilizing, microtubule stabilizing, actin depolymerizing, growth inhibiting, topoisomerase inhibiting, HMG-CoA (3-hydroxy-3-methylglutaryl coenzyme A) reductase inhibiting, purine synthesis inhibiting, pyrimidine synthesis inhibiting, metalloproteinase inhibiting, CDK (cyclin-dependent protein kinase) inhibiting, angiogenesis inhibiting, differentiation enhancing, and immunotherapeutic agents. Anti-arthritic agents include, but are not limited to, anti-inflammatory agents, including non-steroidal anti-inflammatory agents (NSAIDs), analgesics, biologic response modifiers, disease-modifying antirheumatic drugs (DMARDs), anti-metabolic, pro-apoptotic, DNA damaging, microtubule destabilizing, microtubule stabilizing, actin depolymerizing, growth inhibiting, topoisomerase inhibiting, purine synthesis inhibiting, pyrimidine synthesis inhibiting, metalloproteinase inhibiting, CDK inhibiting, or angiogenesis inhibiting agents. NSAIDs include but are not limited to traditional NSAIDs, such as diclofenac potassium, diclofenac sodium, diclofenac sodium with misoprostol, diflunisal, etodolac, fenoprofen, calcium flurbiprofen, ibuprofen, indomethacin, ketoprofen, meclofenamate, sodium mefenamic, acid meloxicam, nabumetone, naproxen, naproxen sodium, oxaprozin, piroxicam, sulindac, and tolmetin sodium, cyclooxygenase-2 (COX-2) inhibitors, such as celecoxib and rofecoxib, salicylates, such as aspirin, choline salicylate, magnesium salicylate, salsalate and sodium salicylate. Analgesics include but are not limited to acetaminophen, acetaminophen with codeine, hydrocodone with acetaminophen, oxycodone, propoxyphene hydrochloride, and tramadol. Biologic response modifiers include but are not limited to etanercept and infliximab. Glucocorticoids include but are not limited to cortisone, dexamethasone, hydrocortisone, methylprednisolone, prednisolone, prednisolone sodium phosphate and prednisone triamcinolone. DMARDs include but are not limited to auranofin (oral gold), azathioprine, cyclophosphamide, cyclosporine, hydroxychloroquine sulfate, leflunomide, methotrexate, minocycline, penicillamine, sulfasalazine, aurothioglucose and gold sodium thiomalate.

Routes of administration are known to one of ordinary skill in the art and include, but are not limited to, oral (e.g. buccal or sublingual), rectal, as a suppository or an enema, topical, parenteral, subcutaneous, transdermal, subdermal, intramuscular, intraperitoneal, intravesicular, intraarticular, intravenous, intradermal, intracranial, intralesional, intrathecal, intratumoral, intraocular, ocular, aerosol, intrapulmonary, intraspinal, intraprostatic, sublingual, placement within cavities of the body, nasal inhalation, pulmonary inhalation, impression into the skin and electroporation, intrauterine, vaginal, into a body cavity, surgical administration at the location of a tumor or internal injury, directly into tumors, into the lumen or parenchyma of an organ, and into bone marrow. Techniques useful in the various forms of administrations mentioned above include but are not limited to, topical application, ingestion, surgical administration, injections, sprays, transdermal delivery devices, osmotic pumps, electrodepositing directly on a desired site, or other means familiar to one of ordinary skill in the art. Sites of application can be external, such as on the epidermis, or internal, for example a joint capsule, a tumor, a gastric ulcer, a surgical field, or elsewhere.

The compositions of the present invention can be applied in the form of creams, gels, solutions, suspensions, liposomes, particles, or other means known to one of skill in the art of formulation and delivery of compositions. Ultrafine particle sizes can be used for inhalation delivery of therapeutics. Some examples of appropriate formulations for subcutaneous administration include but are not limited to implants, depot, needles, capsules, and osmotic pumps. Some examples of appropriate formulations for vaginal administration include but are not limited to creams, suppositories, sponges, gels, foams, and rings. Some examples of appropriate formulations for oral administration include but are not limited to: pills, capsules, liquids, syrups, and suspensions. Some examples of appropriate formulations for transdermal and transmucosal administration include but are not limited to creams, pastes, patches, sprays, and gels. Some examples of appropriate delivery mechanisms for subcutaneous administration include but are not limited to implants, depots, needles, capsules, and osmotic pumps. Formulations suitable for parenteral administration include but are not limited to aqueous and non-aqueous sterile injection solutions which may contain anti-oxidants, buffers, bacteriostats and solutes which render the formulation isotonic with the blood of the intended recipient, and aqueous and non-aqueous sterile suspensions which may include suspending agents and thickening agents. Extemporaneous injection solutions and suspensions may be prepared from sterile powders, granules and tablets commonly used by one of ordinary skill in the art.

The sequences of the invention may be combined with one or more pharmaceutically acceptable carriers or excipients to form a composition. These compositions may conveniently be presented in unit dosage form and may be prepared by conventional pharmaceutical techniques. Such techniques include the step of bringing into association the compositions containing the active ingredient and the pharmaceutical carrier(s) or excipient(s). In general, the formulations are prepared by uniformly and intimately bringing into association the active ingredient with liquid carriers. Preferred unit dosage formulations are those containing a dose or unit, or an appropriate fraction thereof, of the administered ingredient. It should be understood that in addition to the ingredients particularly mentioned above, formulations comprising the compositions of the present invention may include other agents commonly used by one of ordinary skill in the art.

The volume of administration will vary depending on the route of administration. Such volumes are known to one of ordinary skill in the art of administering compositions to animals or humans. Depending on the route of administration, the volume per dose is preferably about 0.001 to 100 ml, more preferably about 0.01 to 50 ml, and most preferably about 0.1 to 30 ml. Preferably, the amount of sequence administered per dose is from about 0.001 to 100 mg/kg of body weight, more preferably from about 0.01 to 10 mg/kg and most preferably from about 0.1 to 5 mg/kg. The sequence, combination of sequences, and/or additional therapeutic agents can be administered in a single dose treatment, in multiple dose treatments or continuously infused on a schedule and over a period of time appropriate to the disease being treated, the condition of the recipient and the route of administration. Moreover, the sequence can be administered before, at the same time as, or after the administration of the therapeutic agent. The particular sequence and the particular therapeutic agent administered, the amount per dose, and the route of administration should be decided by the practitioner using methods known to those skilled in the art and will depend on the disease or condition being treated, for example the type of cancer, the severity of the cancer, the location of the cancer and other clinical factors such as the size, weight and physical condition of the recipient. In addition, various in vitro and in vivo assays may optionally be employed to help identify optimal ranges for sequence and for sequence plus therapeutic agent administration.

A sequence in combination with therapeutic agent, for example a chemotherapeutic agent or an anti-arthritic agent, is administered to an animal, or human, having cancer or arthritis in an amount effective to enhance the anti-neoplastic effect of a chemotherapeutic agent or the anti-arthritic effect of an anti-arthritic agent. Preferably, the amount of therapeutic agent administered per dose is from about 0.001 to 1000 mg/m$^2$ of body surface or from about 0.01 to 1000 mg/kg of body weight, more preferably from about 0.01 to 500 mg/m$^2$ or about 0.01 to 500 mg/kg and most preferably from about 0.1 to 100 mg/m$^2$ or about 0.1 to 100 mg/kg. The particular sequence and the particular therapeutic agent administered, the amount per dose, the dose schedule and the route of administration should be decided by the practitioner using methods known to those skilled in the art and will depend on the type of disease, the severity of the disease, the location of the disease and other clinical factors such as the size, weight and physical condition of the recipient. In addition, various in vitro and in vivo assays may optionally be employed to help identify optimal ranges for sequence and for sequence plus therapeutic agent administration. Various assays useful for this purpose are described in PCT CA00/01467 (WO 01/44465). Additional assays for evaluation of the efficacy of the sequences of the present invention, and for evaluation of the efficacy of these sequences in combination with other therapeutic agents are described by Oncogene Research Products, P.O. Box 12087, La Jolla, Calif., 92039 (Apoptosis Catalog and Technical Guide 2002-2003, especially pages 5-295). Such assays include assays designed to analyze DNA fragmentation, apoptosis, mitochondrial markers, endoplasmic reticulum markers, free nucleosomes, nuclear matrix proteins, detection and activity of numerous caspases and related proteins, including but not limited to caspases 1 through 14, glutathione, superoxide dismutase, members of the bcl-2 family, analysis of the Fas/TNR-R super family, PARP related products, analysis of apoptotic signal transducers, analysis of various signaling receptors including death receptors, Apo2, decoy receptors, analysis of apoptotic membrane proteins, nervous system apoptotic markers, numerous markers for cell cycle and cellular proliferation, mitotic kinases, bromodeoxyuridine assays, and p53 assays. The efficacy of the sequences of the present invention may also be evaluated in terms of other agents, including therapeutic agents, including but not limited to, anti-arthritic agents, or inducers of apoptosis and cell synchronization reagents as described by Oncogene Research Products, P.O. Box 12087, La Jolla, Calif., 92039 (Apoptosis Catalog and Technical Guide 2002-2003, especially pages 99-104 and pages 214-255). Such agents include but are not limited to actinomycin D, amphidocolin, A23187, caffeine, camptothecin, cycloheximide, dexamethasone, doxorubicin, 5-fluorouracil, hydroxyurea, paclitaxel, staurosporine, thymidine, vinblastine, retinoic acid, etoposide, okadaic acid, vincristine and methotrexate.

Various in vitro and in vivo assays and models known to one skilled in the art may be employed for evaluation of the efficacy and optimal dose ranges of sequences, alone or in combination with a therapeutic agent or agents, for the treatment of arthritis. Animal models include but are not limited to adjuvant disease models, oily adjuvant-induced models, microorganisms and their cell wall components-induced models, cartilage components-induced models, transgenic and knockout models, non-immunologic osteoarthritis models, and partial syndromes models, as described in Waxman, B. H., Scand. J. Immunol., 56:12, 2002. Model animals include but are not limited to rats, mice, primates, guinea pigs, and rabbits To determine a cell cycle stage, various assays and procedures known to one skilled in the art may be employed. One such procedure uses a CYCLETEST™ PLUS DNA commercial kit (Becton Dickinson, Franklin Lakes, N.J.). Briefly, nuclei from cells are obtained by dissolving the cell membrane in a nonionic detergent, eliminating the cell cytoskeleton and nuclear proteins with trypsin, digesting the cellular RNA with RNase, and stabilizing the nuclear chromatin with spermine. Propidium iodide is added to the cell nuclei and their fluorescence was analyzed in a flow cytometer equipped with electronic doublet discrimination capability (FACSCalibur, Becton Dickinson, Franklin Lakes, N.J.). Accumulation of cells in $G_0/G_1$, early S (SE), mid S (SM), late S (SL) or $G_2/M$ phases of the cell cycle may be analyzed using MODFIT LT software (Verity Software House Inc., Topsham, Mass.), or other appropriate software.

Various in vitro and in vivo assays may be used to evaluate the influence of the extracellular microenvironment on behavior of normal cells and tumor cells. Such assays may employ MATRIGEL® (Becton Dickinson, Franklin Lakes, N.J.), which is a solubilized basement membrane preparation extracted from the Engelbreth-Holm-Swarm murine sarcoma.

Multicellular spheroids (MS) is an example of a special in vitro assay, in which tumor cells are cultured in a 3-dimensional manner to form a "tumor-like" structure. In this system, there is a reinforcement of cell-cell interactions that mimic microenvironmental conditions of malignant cells in solid tumors in vivo. In this type of assay, no extracellular matrix components are added. Cells cultured in this MS system differ from those in 2-dimensional systems (monolayer culture conditions). Some of these differences are related to structural and functional differentiation of tumor cells, changes in the cell cycle of tumor cells, "multicellular drug resistance", and changes in the diffusion and penetration of drugs throughout layers of tumor cells (reviewed in Green et al., Anticancer Drug Des. 14:153, 1999).

The following examples will serve to further illustrate the present invention without, at the same time, however, constituting any limitation thereof. On the contrary, it is to be clearly understood that resort may be had to various other embodiments, modifications, and equivalents thereof which, after reading the description herein, may suggest themselves to those skilled in the art without departing from the spirit of the invention.

EXAMPLE 1

Preparation of Nucleotide Sequences

Phosphodiester synthetic nucleotide sequences and conjugated 3'-TEG cholesteryl synthetic nucleotide sequences were prepared by Sigma-Genosys (Woodlands, Tex., USA) using Abacus Segmented Synthesis Technology. Sequences terminating at their 3'-ends with TEG cholesteryl were synthesized on TEG CPG support (Glen Research, Sterling, Va., USA). The sequences were dispersed in water or in dimethyl sulfoxide (DMSO) immediately prior to use.

EXAMPLE 2

Cells

All cell lines were obtained from the American Type Culture Collection (ATCC, Rockville, Md.) and were cultured in the medium recommended by the ATCC. Breast cancer cell lines were cultured in medium recommended by the ATCC or described in published articles (Herrera-Gayol and Jothy, Int. J. Exp. Path., 82:193, 2001). Table 1 shows the cell lines, their origin and their biopathological characteristics as described in the literature (Hackett et al., Cancer Inst., 58:1795, 1977;

Price et al., Cancer Res., 50:717, 1990; Thompson et al., J. Cell Physiol., 150:534, 1992; and Peiper M et al., Int. J. Cancer 71: 993, 1997).

TABLE 1

Cell lines

| CELL LINE | DESCRIPTION |
|---|---|
| MEG-01* | Human chronic myelogeneous leukemia cell line |
| EL-4* | Murine T lymphoma cell line |
| HIG-82** | Rabbit synovial cell line |
| MCF-7** | Human, adenocarcinoma of the breast (pleural effusion). Well differentiated. Non-invasive in vitro and in vivo. Non metastatic in vivo. Caspase-3 negative. |
| MDA-MB-231** | Human, adenocarcinoma of the breast (pleural effusion). Poorly differentiated. Invasive in vitro and in vivo. Metastatic. p53 mutated. |
| Hs578T** | Human, carcinosarcoma of the breast (primary tumor). Poorly differentiated. Invasive in vitro and in vivo. Metastatic. p53 mutated. |
| Mpanc-96** | Human, adenocarcinoma of the pancreas (primary tumor). Moderately differentiated adenocarcinoma. Non invasive in vivo. |

*Non-adherent cells.
**Adherent cells.

EXAMPLE 3

Induction of Apoptosis in MEG-01 Cells by SEQ ID NO:5 and SEQ ID NO:6.

Redistribution of plasma membrane phosphatidylserine is a characteristic of cells undergoing apoptosis (Martin et al., J. Exp. Med., 182:1545, 1995). The redistribution of phosphatidylserine in the plasma membrane during apoptosis was measured by flow cytometry using FITC (fluorescein isothiocyanate)-conjugated annexin V (BD Pharmingen, San Diego, Calif.). MEG-01 cells, a human chronic myelogeneous leukemia cell line positive for the Philadelphia chromosome and having a BCR-ABL gene fusion, were incubated at $2.5 \times 10^5$ cells/ml for 48 hours with 5.3, 26.5 and 53.0 µM final concentrations of SEQ ID NO:1, SEQ ID NO:2, SEQ ID NO:5, SEQ ID NO:6 and cholesteryl-TEG phosphoramidite molecule. The percentage of cells in apoptosis after exposure to the SEQ ID NOs:1, 2, 5, 6, or cholesteryl-TEG phosphoramidite treatment is reported in Table 2. The percentage of apoptosis in untreated MEG-01 cells was 12%.

TABLE 2

Percentage of positive cells for phosphatidylserine (cells in apoptosis) in MEG-01 cells

| Composition | Concentration (µM) | | |
|---|---|---|---|
| | 5.3 | 26.5 | 53.0 |
| SEQ ID NO:1 | 12 | 12 | 12 |
| SEQ ID NO:5 | 12 | 27 | 42 |
| SEQ ID NO:2 | 12 | 12 | 12 |
| SEQ ID NO:6 | 13 | 22 | 39 |
| cholesteryl-TEG phosphoramidite | 12 | 12 | 12 |

As shown in Table 2, SEQ ID NO:1, SEQ ID NO:2 and cholesteryl-TEG phosphoramidite are inactive against MEG-01. Unexpectedly the addition of a cholesteryl-TEG phosphoramidite at the 3'-end of SEQ ID NO:1, resulting in SEQ ID NO:5, and at the 3'-end of SEQ ID NO:2, resulting in SEQ ID NO:6, conferred to these inert oligonucleotides the capacity to induce apoptosis in MEG-01 cells as measured by the translocation of phosphatidylserine at the cell surface.

EXAMPLE 4

Induction of Apoptosis in EL-4 Cells by SEQ ID NO:7

EL-4 cells, a murine T lymphoma cell line, were incubated at $2.5 \times 10^5$ cells/ml for 24 hours with 0.53, 5.3 and 53.0 µM concentrations of SEQ ID NO:3, SEQ ID NO:7 or cholesteryl-TEG phosphoramidite. The percentage of cells in apoptosis after exposure to SEQ ID NO:3, SEQ ID NO:7 or cholesteryl-TEG phosphoramidite treatment is reported in Table 3. The percentage of apoptosis in untreated EL-4 cells was 7%.

TABLE 3

Percentage of positive cells for phosphatidylserine (cells in apoptosis) in EL-4 cells

| Composition | Concentration (µM) | | |
|---|---|---|---|
| | 0.53 | 5.3 | 53.0 |
| SEQ ID NO:3 | 7 | 7 | 7 |
| SEQ ID NO:7 | 8 | 11 | 49 |
| TEG cholesteryl-phosphoramidite | 7 | 7 | 7 |

As shown in Table 3, neither SEQ ID NO:3 nor cholesteryl-TEG phosphoramidite caused apoptosis in EL-4 cells. Unexpectedly, the addition of a cholesteryl-TEG phosphoramidite at the 3'-end of SEQ ID NO:3, resulting in SEQ ID NO:7, conferred to this inert oligonucleotide the capacity to induce apoptosis in EL-4 cells as measured by the translocation of phosphatidylserine at the cell surface.

EXAMPLE 5

Activation of Caspase 3 by SEQ ID NO:7

EL-4 cells ($2.5 \times 10^5$ cells/ml) were incubated for 72 hrs with 0 µM (control), 53 µM of SEQ ID NO:3 or 53 µM of SEQ ID NO:7. After incubation, both control and treated cells were washed, fixed, permeabilized and incubated with a Phycoerythrin (PE)-conjugated antibody that recognizes the active catalytic unit of caspase 3 (Clone: C92-605; BD Pharmingen, San Diego, Calif., USA) using the conditions recommended by the manufacturer. Fluorescence associated with active caspase 3 was analyzed by flow cytometry on a FACSCALIBUR using the program CellQUEST (both from Becton Dickinson, San Jose, Calif., USA). The percentage of cells containing active caspase 3 in EL-4 cells treated with 53 µM of sequences is reported in the Table 4.

TABLE 4

Percentage of cells containing active caspase 3 in EL-4 cells

| Treatment | Percentage of cells containing activated caspase-3 |
|---|---|
| Untreated EL-4 cells | 3 |
| EL-4 cells + 53 µM of SEQ ID NO:3 | 4 |
| EL-4 cells + 53 µM of SEQ ID NO:7 | 38 |

As shown in Table 4, SEQ ID NO:3 was inactive against EL-4. Unexpectedly the addition of a cholesteryl-TEG phosphoramidite at the 3'-end of SEQ ID NO:3, resulting in SEQ ID NO:7 conferred to this inert oligonucleotide the capacity to induce apoptosis as measured by the activation of caspase-3.

EXAMPLE 6

Cleavage of Poly(ADP-ribose) Polymerase by SEQ ID NO:7

EL-4 cells ($2.5 \times 10^5$ cells/ml) were incubated for 72 h with 0 μM (control), 53 μM of SEQ ID NO:3 or 53 μM of SEQ ID NO:7. After incubation, both control and treated cells were washed, fixed, permeabilized and incubated with an FITC-conjugated antibody that recognizes specifically the 85 kDa fragments of cleaved PARP (BioSource, Camarillo, Calif., USA) using the conditions recommended by the manufacturer. Fluorescence associated with cleaved PARP was analyzed by flow cytometry on a FACSCalibur using the program CellQUEST (both from Becton Dickinson). The percentage of cells containing cleaved PARP in EL-4 cells treated with 53 μM final concentration of sequences is shown in Table 5.

TABLE 5

Percentage of cells containing cleaved PARP in EL-4 cells

| Treatment | Percentage of cells containing cleaved PARP |
| --- | --- |
| Untreated EL-4 cell | 1 |
| EL-4 cells + 53 μM of SEQ ID NO:3 | 1 |
| EL-4 cells + 53 μM of SEQ ID NO:7 | 84 |

As shown in Table 5, SEQ ID NO:3 was inactive against EL-4. Unexpectedly the addition of a cholesteryl-TEG phosphoramidite at the 3'-end of SEQ ID NO:3, resulting in SEQ ID NO:7, conferred to this inert oligonucleotide the capacity to induce apoptosis as measured by cleavage of PARP.

EXAMPLE 7

Effect of SEQ ID NO:2, SEQ ID NO:3, SEQ ID NO:4, SEQ ID NO:6, SEQ ID NO:7, and SEQ ID NO:8 on Proliferation of Synovial Cells Adherent HIG-82 cells, a synovial cell line, were incubated at $10 \times 10^5$ cells/ml for 48 hours with 53 μM (final concentration) of SEQ ID NO:2, SEQ ID NO:3, SEQ ID NO:4, SEQ ID NO:6, SEQ ID NO:7, or SEQ ID NO:8. Cellular proliferation was measured using dimethylthiazol-diphenyl-tetrazolium (MTT) reduction (Mosman et al., J. Immunol. Methods 65:55, 1983). MTT was measured at a wavelength of 570 nm using a multiple spectrophotometer reader (ELX800, Bio-TEK, Instruments Inc., Winooski, Vt.). The percentage of inhibition, calculated as $$\frac{\text{control absorbance} - \text{treatment absorbance}}{\text{control absorbance}} \times 100\%,$$

of HIG-82 cell proliferation is shown in Table 6.

TABLE 6

Inhibition of HIG-82 cell proliferation (%)

| TREATMENT (53 μM) | inhibition (%) |
| --- | --- |
| SEQ ID NO:2 | 6% |
| SEQ ID NO:6 | 75% |

TABLE 6-continued

Inhibition of HIG-82 cell proliferation (%)

| TREATMENT (53 μM) | inhibition (%) |
| --- | --- |
| SEQ ID NO:3 | 0% |
| SEQ ID NO:7 | 53% |
| SEQ ID NO:4 | −7% |
| SEQ ID NO:8 | 64% |

As shown in Table 6, SEQ ID NO:2, SEQ ID NO:3 and SEQ ID NO:4 did not inhibit proliferation of synovial HIG-82 cells. Unexpectedly the addition of a cholesteryl-TEG phosphoramidite at the 3'-ends of SEQ ID NO:2, SEQ ID NO:3, and SEQ ID NO:4, resulting in SEQ ID NOs:6, 7, and 8, respectively, conferred the capacity to inhibit the cellular proliferation of HIG-82 cells.

EXAMPLE 8

Induction of Apoptosis in Proliferating Synovial Cells by SEQ ID NO:5 and SEQ ID NO:6

Adherent HIG-82 cells were incubated at $1.0 \times 10^5$ cells/ml for 48 hours with 53 μM final concentration of SEQ ID NO:1, SEQ ID NO:2, SEQ ID NO:5 or SEQ ID NO:6. Since phosphatidylserine/annexin V detection of apoptosis was not reliable after adherent cell harvesting techniques, such as trypsinization (van Engeland, Cytometry, 31:1, 1998), apoptosis in HIG-82 cells was evaluated using flow cytometry by the detection of fragmented DNA by terminal deoxynucleotidyl transferase enzyme-mediated bromodeoxyuridine triphosphate-biotin nick end-labeling (TUNEL) using a commercial assay (APO-BRDU™ kit; BD Pharmingen). The percentage of cells containing nuclear DNA fragmentation was determined. After 24 hours, untreated HIG-82 cells were essentially negative for nuclear DNA fragmentation.

TABLE 7

Percentage of cells containing DNA fragmentation (cells in apoptosis) in HIG-82 cells

| Treatment (53 μM) | Percentage of cells containing DNA fragmentation |
| --- | --- |
| SEQ ID NO:1 | 1 |
| SEQ ID NO:5 | 17 |
| SEQ ID NO:2 | 1 |
| SEQ ID NO:6 | 18 |

As shown in Table 7, SEQ ID NO:1 and SEQ ID NO:2 were inactive against exponentially growing synovial cells. Unexpectedly the addition of a cholesteryl-TEG phosphoramidite at the 3'-end of SEQ ID NO:1 and SEQ ID NO:2, resulting in SEQ ID NO:5 and SEQ ID NO:6, respectively, conferred the capacity to induce apoptosis in HIG-82 cells as measured by the percentage of cells showing fragmented nuclear DNA.

EXAMPLE 9

Induction of Cell Cycle Arrest by SEQ ID NO:6

Exponentially growing MEG-01 cells ($2 \times 10^5$ cells/ml) were incubated for 24 h with 0 μM (control), 53 μM of SEQ ID NO:2 or 53 μM of SEQ ID NO:6. The cells were collected, centrifuged, and cell cycle stage was determined.

TABLE 8

Induction of cell cycle arrest in MEG-01 leukemia cells by SEQ ID NO:6

| Treatment (53 μM) | % of cells in phase | | |
|---|---|---|---|
| | $G_0/G_1$ + SE | SM | SL + $G_2$/M |
| Untreated cells | 71.4 | 10.8 | 17.8 |
| SEQ ID NO:2 | 68.6 | 11.6 | 19.8 |
| SEQ ID NO:6 | 51.6 | 6.5 | 41.9 |

As shown in Table 8, SEQ ID NO:2 was inactive against MEG-01 when compared to untreated control cells. Unexpectedly the addition of a cholesteryl-TEG phosphoramidite at the 3'-end of SEQ ID NO:2, resulting in SEQ ID NO:6, conferred the capacity to induce cell cycle arrest at the SL+$G_2$/M phase in MEG-01 cells.

EXAMPLE 10

Effect of SEQ ID NO:3 and SEQ ID NO:7 on Cellular Proliferation of Human Breast Cancer Cells.

Either $20 \times 10^3$ MDA-MB-231 (MDA-231) or Hs578T cells were plated into individual wells of 24-well plates in regular culture medium (RCM) presence or absence (control) of 53 μM (final concentration) of SEQ ID NO:3, SEQ ID NO:7, 53 μM cholesteryl-TEG phosphoramidite, or corresponding control media (regular culture medium (RCM) for SEQ ID NO:3, RCM with the same amount of water as the amount added with the SEQ ID NO:7, and RCM with the same amount of acetonitrile as the amount added with cholesteryl-TEG phosphoramidite). Cells were cultured for 72 hrs, removed with trypsin and counted with an hemocytometer using the Trypan blue exclusion technique. Results of three independent assays (mean and standard deviation (s.d.) of percentage of changes compared to controls) are shown in Table 9.

TABLE 9

Percentage of changes in cellular proliferation* of MDA-231 and Hs578T human breast cancer cells cultured for 3 days.

| | SEQ ID NO:3 | SEQ ID NO:7 | cholesteryl-TEG phosphoramidite | *P value |
|---|---|---|---|---|
| MDA-231 | +6.9 ± 5 | −97.9 ± 2.5 | −2.3 ± 15.9 | <0.01 |
| Hs578T | −6.5 ± 5 | −91.8 ± 10.5 | +13 ± 9.2 | <0.01 |

*"positive +" changes represent stimulation of proliferation and "negative −" changes represent inhibition of proliferation calculated as $$\frac{\text{control absorbance} - \text{treatment absorbance}}{\text{control absorbance}} \times 100\%$$

**p value obtained by Dunnett's multiple comparison test after Repeated Measured Analysis of variance (RM ANOVA).

As shown in Table 9, SEQ ID NO:3 and cholesteryl-TEG phosphoramidite did not significantly affect cellular proliferation. Unexpectedly, the addition of cholesteryl-TEG phosphoramidite at the 3' end of SEQ ID NO:3, resulting in SEQ ID NO:7, conferred the capacity to inhibit cellular proliferation of two highly aggressive human breast cancer cells.

EXAMPLE 11

Changes in 3-dimensional Structure Formation Induced by SEQ ID NO:5 in MATRIGEL® Outgrowth Experiments MCF-7, MDA-MB-231 (MDA-231), Hs578T and Mpanc-96 cells were cultured separately in regular culture medium, trypsinized, and counted. $100 \times 10^3$ of MDA-231 cells, $100 \times 10^3$ of Hs578T cells, $150 \times 10^3$ of MCF-7 cells and $150 \times 10^3$ of Mpanc-96 cells were separately pre-incubated for 1 hr at 37° C. in a final concentration of 53 μM of SEQ ID NO:1, 53 μM of SEQ ID NO:5 or RCM, and plated on top of MATRIGEL®-coated plates (MATRIGEL® Basement membrane matrix coated cellware 24-well plate,) for 3 days. Plates were fixed with 10% formalin. Digital photographs of the cells in the 24-well plates were taken using a Nikon Coolpix 990 digital camera (Nikon Corporation, Tokyo, Japan) connected to a Nikon inverted microscope model TMS. While SEQ ID NO:1 did not change cell morphology, SEQ ID NO:5 prevented the formation of 3-dimensional structures similar to those formed when cells were cultured in the regular culture medium on MATRIGEL® (see FIG. 1).

As shown in FIG. 1, SEQ ID NO:1 was inactive while, unexpectedly, the addition of cholesteryl-TEG phosphoramidite at the 3'-end of SEQ ID NO:1, resulting in SEQ ID NO:5, conferred the capability to prevent formation of 3-dimensional structures similar to those formed when cells were cultured in regular culture medium on MATRIGEL®. It is believed that SEQ ID NO:5 interfered with cell-extracellular matrix interactions thereby modulating cell-cell and cell-extracellular matrix adhesion mechanisms.

EXAMPLE 12

Changes in 3-dimensional Structure Formation Induced by SEQ ID NO:8 in MATRIGEL® (Beckton Dickinson, Franklin Lakes, N.J.) Outgrowth Experiments MDA-MB-231 (MDA-231) and Hs578T were cultured in regular culture medium, trypsinized and counted. $100 \times 10^3$ of MDA-MB-231 cells or $100 \times 10^3$ of Hs578T cells, were separately pre-incubated for 1 hr at 37° C. in a final concentration of 53 μM of SEQ ID NO:4, 53 μM of SEQ ID NO:8 or RCM and plated on MATRIGEL®-coated plates for 3 days. Plates were fixed with 10% formalin. Digital photographs of the cells in the 24-well plates were taken using a Nikon Coolpix 990 digital camera (Nikon Corporation, Tokyo, Japan) connected to a Nikon inverted microscope model TMS. While SEQ ID NO:4 did not change the cellular morphology, SEQ ID NO:8 disrupted the growth pattern of tumor cells plated on MATRIGEL® (see FIG. 2).

As shown in FIG. 2, SEQ ID NO:4 was inactive while, unexpectedly, the addition of cholesteryl-TEG phosphoramidite at the 3'-end of SEQ ID NO:4, resulting in SEQ ID NO:8, conferred the capability to prevent formation of 3-dimension structures, similar to those formed when cells were cultured in the regular culture medium on MATRIGEL®-coated wells. It is believed that SEQ ID NO:8 interfered with cell-extracellular matrix interactions thereby modulating interactions between tumor cells and the ECM components.

EXAMPLE 13

Changes in 3-dimensional Structure Formation of MCF-7 Cells Induced by SEQ ID NO:7 in MATRIGEL® Outgrowth Experiments MCF-7 cells were cultured in regular culture medium (RCM), trypsinized and counted. $150 \times 10^3$ of MCF-7 cells, in wells of 24-well plates coated with 350 μl of MATRIGEL®. After the formation of 3-dimensional structures during 48 hrs without any treatment, the medium was changed and the structures were exposed to a final concentration of 53 μM of SEQ ID NO:3, 53 μM of SEQ ID NO:7, 53 μM of cholesteryl-TEG phosphoramidite, RCM or their respective control media (RCM with water, RCM with DMSO, or RCM with acetonitrile). The treatments were repeated every 3-4 days until a maximum time in culture of 19-20 days. The experiment was repeated three times. Digital photographs of the cells in the 24-well plates were taken using a Nikon Coolpix 990 digital camera connected to a Nikon inverted microscope model TMS. While the respective control media (data not shown), SEQ ID NO:3 and cholesteryl-TEG phosphoramidite did not affect the 3-dimensional structures compared to controls, SEQ ID NO:7 disrupted the growth pattern of the structures thereby affecting cell-cell and cell-extracellular matrix interactions (see FIG. 3).

As shown in FIG. 3, SEQ ID NO:3 and cholesteryl-TEG phosphoramidite were inactive while, unexpectedly, the addition of cholesteryl-TEG phosphoramidite at the 3'-end of SEQ ID NO:3, resulting in SEQ ID NO:7, conferred the capability to disrupt pre-formed 3-dimensional structures.

EXAMPLE 14

Changes in 3-dimensional Structure Formation of MDA-MB-231 Cells Induced by SEQ ID NO:7 in MATRIGEL® Outgrowth Experiments The MDA-MB-231 (MDA-231) cells were cultured in regular culture medium, trypsinized and counted. $100 \times 10^3$ of MDA-231 cells were plated in regular culture medium (RCM), in wells of 24-well plates coated with 350 µl of MATRIGEL®. After the formation of 3-dimensional structures during 48 hrs without any treatment, the medium was changed, and structures were exposed to a final concentration of 53 µM of SEQ ID NO:3, 53 µM of SEQ ID NO:7, 53 µM of cholesteryl-TEG phosphoramidite, RCM, or their respective control media (RCM with water, RCM with DMSO or RCM with acetonitrile). The treatments were repeated every 3-4 days until a maximum time in culture of 17-21 days. The experiment was repeated three times. Digital photographs of the cells in the 24-well plates were taken using a Nikon Coolpix 990 digital camera connected to a Nikon inverted microscope model TMS. While the respective control media (data not shown), SEQ ID NO:3 and cholesteryl-TEG phosphoramidite did not affect the 3-dimensional structures, being similar to the structures cultured in the RCM (negative control medium), SEQ ID NO:7 disrupted the growth pattern of the structures thereby affecting cell-cell and cell-extracellular matrix interactions (see FIG. 4).

As shown in FIG. 4, SEQ ID NO:3 and cholesteryl-TEG phosphoramidite were inactive while, unexpectedly, the addition of cholesteryl-TEG phosphoramidite at the 3'-end of SEQ ID NO:3, resulting in SEQ ID NO:7, conferred the capability to disrupt 3-dimensional structures by interfering with cell-cell and cell-extracellular matrix interactions.

EXAMPLE 15

Changes in Cell Cycle Induced by SEQ ID NO:7 when the Hs578T cells were Cultured as Multicellular Spheroids About $100 \times 10^3$ Hs578T cells per spheroid were cultured in presence of 53 µM final concentration of SEQ ID NO:3, SEQ ID NO:7, 53 µM final concentration of cholesteryl-TEG phosphoramidite (cholTEG) or corresponding control media (regular culture medium (RCM), RCM with the same amount of water (RCMW) as the amount added with the SEQ ID NO:7, and RCM with the same amount of acetonitrile (RCMA) as the amount added with cholesteryl-TEG phosphoramidite). Five spheroids per each experimental condition were cultured for 72 hrs. Afterwards, cell cycle progression was evaluated by propidium iodide (PI) staining (Calbiochem, Novabiochem Corporation, San Diego, Calif.) using a FACScalibur flow cytometer (Becton Dickinson, Franklin Lakes, N.J.). Changes in the percentage of cells in the different phases of the cell cycle were analyzed using MODFIT LT software (Verity Software House Inc). Results are shown in FIG. 5.

As shown in FIG. 5, SEQ ID NO:3, cholesteryl-TEG phosphoramidite or control media did not significantly modify cell cycle progression compared to those spheroids exposed to the regular culture medium alone. Unexpectedly, exposure to SEQ ID NO:7 increased the percentage of cells in $G_2M$ and S-phase and decrease the percentage of cells in $G_0/G_1$ ($p<0.05$ by $\chi$-square test). The addition of cholesteryl-TEG phosphoramidite conferred to an inactive oligonucleotide tested in the MS assay the capacity to modify cell cycle progression in a complex 3-dimensional system that mimics several biopathological characteristics of in vivo tumors.

EXAMPLE 16

Changes in the Release of Nuclear Mitotic Apparatus Protein (NuMA) by MDA-MB-231 Human Breast Cancer Cells when Incubated with SEQ ID NO:5

MDA-MB-231 cells were cultured as monolayers in respective control media, with 53 µM final concentration of SEQ ID NO:1 or 53 µM final concentration of SEQ ID NO:5 for 72 hrs. The release of nuclear mitotic apparatus protein (NuMA) was used as a measure of apoptosis. NuMA was determined using a commercial (ELISA kit (Oncogene, Cambridge, Mass.) following the manufacturer's protocol. Results are shown in Table 10 and are expressed as the percentage increase in NuMA release compared to respective controls based on optical density measurements.

TABLE 10

Changes in the release of nuclear mitotic apparatus protein (NuMA) in MDA-MB-231 human breast cancer cells

| SEQUENCE | NuMA release compared to controls (%) |
|---|---|
| SEQ ID NO:1 | +5% |
| SEQ ID NO:5 | +430% |

As shown in Table 10, the release of nuclear mitotic apparatus protein (NuMA) increased by 430% after cells were incubated with SEQ ID NO:5. Unexpectedly, the addition of cholesteryl-TEG phosphoramidite to the 3' end of SEQ ID NO:1, resulting in SEQ ID NO:5, conferred the capacity to induce apoptosis.

EXAMPLE 17

Changes in the Release of Nuclear Mitotic Apparatus Protein (NuMA) by Hs578T Human Breast Cancer Cells when Incubated with SEQ ID NO:6

Hs578T cells were cultured as monolayer in negative control conditions or with 53 µM final concentraition of SEQ ID NO:2, 53 µM of SEQ ID NO:6 for 72 hrs. The release of nuclear mitotic apparatus protein (NuMA) was used as a measure of apoptosis. NuMA was determined using a commercial ELISA kit following the manufacturer's protocol. Results are shown in Table 11 and are expressed as the percentage increase in NuMA release compared to control conditions based on optical density measurements.

TABLE 11

Changes in the release of nuclear mitotic apparatus protein (NuMA) by Hs578T human breast cancer cells

| SEQUENCE | NuMA release compared to control (%) |
|---|---|
| SEQ ID NO:2 | +8% |
| SEQ ID NO:6 | +288% |

As shown in Table 11, the release of nuclear mitotic apparatus protein (NuMA) increased by 288% after cells were incubated with SEQ ID NO:6 Unexpectedly, the addition of cholesteryl-TEG phosphoramidite to the 3' end of SEQ ID NO:2 conferred to an inactive oligonucleotide the capacity to induce apoptosis.

EXAMPLE 18

Effect of SEQ ID NO:1, SEQ ID NO:2, SEQ ID NO:5, and SEQ ID NO:6 on MEG-01 Cells in Athymic Nude Mice MEG-01 cells are inoculated subcutaneously into athymic nude mice as previously described (Takeo et al., Leukemia 7:1286, 1993). The mice are divided into 13 groups of 10 mice. On day 0, group 1 mice receive saline, group 2 mice receive 1 mg/kg SEQ ID NO:1, group 3 mice receive 10 mg/kg SEQ ID NO:1, group 4 mice receive 100 mg/kg SEQ ID NO:1, group 5 mice receive 1 mg/kg SEQ ID NO:2, group 6 mice receive 10 mg/kg SEQ ID NO:2, group 7 mice receive 100 mg/kg SEQ ID NO:2, group 8 mice receive 1 mg/kg SEQ ID NO:5, group 9 mice receive 10 mg/kg SEQ ID NO:5, group 10 mice receive 100 mg/kg SEQ ID NO:5, group 11 mice receive 1 mg/kg SEQ ID NO:6, group 12 mice receive 10 mg/kg SEQ ID NO:6 and group 13 mice receive 100 mg/kg SEQ ID NO:6 After 4 weeks of treatment, the mice are sacrificed and tumor mass is determined. Mice in groups 8-13 have less tumor mass than mice in groups 1-7. Mice in groups 8-13 display less tumor mass in a dose-dependent fashion.

EXAMPLE 19

Effect of SEQ ID NO:3 and SEQ ID NO: 7 on Growth of Lymphoma Cells in Mice

EL-4 murine T lymphoma cells are implanted subcutaneously into C57/BL6 mice as previously described (Krawczyk et al., Cancer Immunol. Immunother. 40:347, 1995). The mice are divided into 7 groups of 10 mice. On day 0, group 1 mice receive saline, group 2 mice receive 1 mg/kg SEQ ID NO:3, group 3 mice receive 10 mg/kg SEQ ID NO:3, group 4 mice receive 100 mg/kg SEQ ID NO:3, group 5 mice receive 1 mg/kg SEQ ID NO:7, group 6 mice receive 10 mg/kg SEQ ID NO:7, group 7 mice receive 100 mg/kg SEQ ID NO:7. After 4 weeks of treatment, the mice are sacrificed and tumor mass is determined. Groups 5-7 have less tumor mass than mice in groups 1-4. Mice in groups 5-7 display less tumor mass in a dose-dependent fashion.

EXAMPLE 20

Effect of SEQ ID NO:1, SEQ ID NO:2, SEQ ID NO:5 and SEQ ID NO:6 on Rats with Streptococcal Cell Wall-induced Arthritis Streptococcal cell wall-induced arthritis in LEW/N rats resembles a localized neoplasm consisting of, in part, of a proliferative and invasive population of fibroblast-like synovial cells (Yocum et al., Am. J. Pathol. 132:38, 1988). The arthritis is induced in LEW/N rats by intra-articular injection of streptocococcal cell wall (SCW) from group A Streptococcus pyogenes. The rats are divided into 13 groups of 10 rats. On day 0, group 1 rats receive SCW, group 2 rats receive SCW+1 mg/kg SEQ ID NO:1, group 3 rats receive SCW+10 mg/kg SEQ ID NO:1, group 4 rats receive SCW+100 mg/kg SEQ ID NO:1, group 5 rats receive SCW+1 mg/kg SEQ ID NO:2, group 6 rats receive SCW+10 mg/kg SEQ ID NO:2, group 7 rats receive SCW+100 mg/kg SEQ ID NO:2, group 8 rats receive SCW+1 mg/kg SEQ ID NO:5, group 9 rats receive SCW+10 mg/kg SEQ ID NO:5, group 10 rats receive SCW+100 mg/kg SEQ ID NO:5, group 11 rats receive SCW+1 mg/kg SEQ ID NO:6, group 12 rats receive SCW+10 mg/kg SEQ ID NO:6, group 13 rats receive SCW+SEQ ID NO:6. The joint inflammation is monitored daily for two weeks. Group 8-13 rats show less inflammation than group 1-7 rats. Rats in groups 8-13 have less inflammation in a dose-dependent fashion.

EXAMPLE 21

Effect of Sequences Conjugated with TEG Cholesteryl on Cell Morphology and Cell Cycle when Cancer Cells are Grown as Monolayers, on MATRIGEL® or as Multicellular Spheroids Different types of malignant cell lines from breast, pancreas, colon, ovary and prostate are cultured as monolayers, on MATRIGEL®-coated wells or as multicellular spheroids (MS). Cells are treated individually with oligonucleotide sequences of different lengths (3 and 6 bases) with or without conjugated cholesteryl-TEG phosphoramidite for at least 1-3 days. Such sequences include, but are not limited to SEQ ID NO:1, SEQ ID NO:5, SEQ ID NO:2, SEQ ID NO:6, SEQ ID NO:3, SEQ ID NO:7; SEQ ID NO:4, or SEQ ID NO:8. Cell proliferation/necrosis (measured by Trypan blue exclusion), apoptosis (measured by flow cytometry, release of nuclear mitotic apparatus protein (NuMA), detection of fragmented DNA by terminal deoxynucleotidyl transferase enzyme-mediated bromodeoxyuridine triphosphate-biotin nick end-labeling (TUNEL)), cell cycle progression studied by flow cytometry (PI staining) and morphology of tumor cells plated on MATRIGEL®-coated wells or as multicellular spheroids (MS) are studied.

Oligonucleotide sequences conjugated with cholesteryl-TEG phosphoramidite increase cell death (necrosis and apoptosis), modify cell cycle progression when cells are cultured as MS or on MATRIGEL®-coated plates, and change cell morphology when cells are cultured as MS or on MATRIGEL®-coated wells. Unconjugated oligonucleotides are inactive.

EXAMPLE 22

Effect of SEQ ID NO:3 and SEQ ID NO:7 on MDA-MB-231 Xenotransplanted Tumors

MDA-MB-231 cells are xenotransplanted subcutaneously into nude mice. The mice are divided into 7 groups of 10 mice. After the tumors reach 5 mm in diameter, group 1 mice receive saline, group 2 mice receive 0.5 mg/kg SEQ ID NO:3, group 3 mice receive 5 mg/kg SEQ ID NO:3, group 4 mice receive 50 mg/kg SEQ ID NO:3, group 5 mice receive 0.5 mg/kg SEQ ID NO:7, group 6 mice receive 5 mg/kg SEQ ID NO:7, group 7 mice receive 50 mg/kg SEQ ID NO:7. Treatments are given intravenously every 3 days for 6 doses maximum. Mice are sacrificed when tumor reach 1 cm in diameter, at any sign of distress or at the end of the study (3 months from cell injection). Complete autopsies are performed. Tumor mass, presence of invasion and metastasis are determined. Groups 5-7 have less tumor mass than group 1-4 mice. Mice in groups 5-7 display less tumor mass in a dose-dependent fashion.

EXAMPLE 23

Effect of SEQ ID NO:3 and SEQ ID NO: 7 on MDA-MB-231 Xenotransplanted Tumors

Breast cancer MDA-MB-231 cells are xenotransplanted subcutaneously in nude mice ($1\times10^7$ cells). The mice are divided into 7 groups of 10 mice. After the tumors reach 5 $mm^2$ in diameter, group 1 mice receive saline, group 2 mice receive 0.4 mg/kg SEQ ID NO:3, group 3 mice receive 4 mg/kg SEQ ID NO:3, group 4 mice receive 40 mg/kg SEQ ID NO:3, group 5 mice receive 0.4 mg/kg SEQ ID NO:7, group 6 mice receive 4 mg/kg SEQ ID NO:7, group 7 mice receive 40 mg/kg SEQ ID NO:7. Treatments are given intravenously every 3 days for 6 doses maximum. Mice are sacrificed when tumor reach 1 cm in diameter, at any sign of distress or at the end of the study (3 months from cell injection). Complete autopsies are performed. Tumor mass, presence of invasion and metastasis are determined. Groups 5-7 have less tumor mass and metastasis than group 1-4 mice. Mice in groups 5-7 display less tumor mass and metastasis in a dose-dependent fashion.

All patents, publications and abstracts cited above are incorporated herein by reference in their entirety. It should be understood, of course, that the foregoing relates only to preferred embodiments of the present invention and that numerous modifications or alterations may be made therein without departing from the spirit and the scope of the invention as set forth in the appended claims.

We claim:

1. A composition comprising a 5'-OH, 3'-TEG cholesteryl synthetic sequence, wherein the sequence is SEQ ID NO:5, SEQ ID NO:6, SEQ ID NO:7 or SEQ ID NO:8, and wherein the composition is effective to treat cancer or arthritis.

2. The composition of claim 1, wherein the sequence is SEQ ID NO:5.

3. The composition of claim 1, wherein the sequence is SEQ ID NO:6.

4. The composition of claim 1, wherein the sequence is SEQ ID NO:7.

5. The composition of claim 1, wherein the sequence is SEQ ID NO:8.

6. The composition of claim 1, further comprising a pharmaceutically acceptable carrier.

7. The composition of claim 1, further comprising a therapeutic agent.

8. A method for inhibiting cell proliferation, inducing cell cycle arrest, inducing apoptosis, activating caspase, inducing cleavage of poly(ADP ribose) polymerase, modulating extracellular matrix-cell interaction, or a combination therof, comprising administering to an animal or a human the composition of claim 1 and a pharmaceutically acceptable carrier, in an amount effective to induce a response in a cell in the animal or the human, wherein the response is selected from the group consisting of inhibition of cell proliferation, induction of cell cycle arrest, induction of apoptosis, activation of caspase, cleavage of poly(ADP ribose) polymerase, modulation of extracellular matrix-cell interaction, or a combination therof.

9. The method of claim 8, wherein the sequence is SEQ ID NO:5.

10. The method of claim 8, wherein the sequence is SEQ ID NO:6.

11. The method of claim 8, wherein the sequence is SEQ ID NO:7.

12. The method of claim 8, wherein the sequence is SEQ ID NO:8.

13. The method of claim 8, wherein the cell is a cancer cell or a synovial cell.

14. The method of claim 13, wherein the response is induction of cell cycle arrest in the cancer cell or the synovial cell.

15. The method of claim 13, wherein the response is induction of apoptosis in the cancer cell or the synovial cell.

16. The method of claim 13, wherein the response is activation of caspase in the cancer cell or the synovial cell.

17. The method of claim 13, wherein the response is cleavage of poly(ADP ribose) polymerase in the cancer cell or the synovial cell.

18. The method of claim 13, wherein the response is inhibition of cellular proliferation in the cancer cell or the synovial cell.

19. The method of claim 13, wherein the response is modulation of extracellular matrix-cell interactions in the cancer cell or the synovial cell.

20. The method of claim 8, wherein the animal or the human has cancer or arthritis.

21. The method of claim 20, wherein the disease is cancer.

22. The method of claim 21, wherein the cancer is lymphoma, leukemia, or breast cancer.

23. The method of claim 20, wherein the disease is arthritis.

24. The method of claim 8, wherein the effective amount is from about 0.001 to about 100 mg/kg of body weight.

25. The method of claim 24, wherein the effective amount is from about 0.01 to about 10 mg/kg of body weight.

26. The method of claim 24, wherein the effective amount is from about 0.1 to about 5 mg/kg of body weight.

27. The method of claim 8, wherein the composition further comprises a therapeutic agent.

28. The method of claim 27, wherein the therapeutic agent is an anti-neoplastic agent, an anti-arthritic agent, an anti-inflammatory agent, an anti-autoimmune agent, an anti-degenerative agent, a Fas modulating agent, a FasL modulating agent, radiation therapy, or a combination thereof.

29. A method for inhibiting cell proliferation, inducing cell cycle arrest, inducing apoptosis, activating caspase, inducing cleavage of polv(ADP ribose) polymerase, modulating extracellular matrix-cell interaction, or a combination therof, comprising administering in vitro to a cell the composition of claim 1 and a pharmaceutically acceptable carrier, in an amount effective to induce a response in the cell, wherein the response is selected from the group consisting of inhibition of cell proliferation, induction of cell cycle arrest, induction of apoptosis, activation of caspase, cleavage of polv(ADP ribose) polymerase, modulation of extracellular matrix-cell interaction, or a combination thereof.

* * * * *

UNITED STATES PATENT AND TRADEMARK OFFICE
CERTIFICATE OF CORRECTION

PATENT NO. : 7,635,686 B2  Page 1 of 1
APPLICATION NO. : 10/264280
DATED : December 22, 2009
INVENTOR(S) : Nigel C. Phillips, Mario C. Filion and Andréa C. Herréra Gayol It is certified that error appears in the above-identified patent and that said Letters Patent is hereby corrected as shown below:

Title page item [75] Inventors:

Please change the spelling of "Andrea" to --Andréa--

In the Claims:

Claim 29, Line 20. Please change "polv(ADP ribose)" to --poly(ADP ribose)--

Claim 29, Line 27. Please change "polv(ADP ribose)" to --poly(ADP ribose)--

Signed and Sealed this

Thirteenth Day of April, 2010

David J. Kappos
*Director of the United States Patent and Trademark Office*

UNITED STATES PATENT AND TRADEMARK OFFICE
CERTIFICATE OF CORRECTION

PATENT NO. : 7,635,686 B2  
APPLICATION NO. : 10/264280  
DATED : December 22, 2009  
INVENTOR(S) : Nigel C. Phillips, Mario C. Filion and Andréa C. Herréra Gayol It is certified that error appears in the above-identified patent and that said Letters Patent is hereby corrected as shown below:

Title page item [75] Inventors:

Please change the spelling of "Andrea" to --Andréa--

In the Claims:

Column 28, Claim 29, Line 20. Please change "polv(ADP ribose)" to --poly(ADP ribose)--

Column 28, Claim 29, Line 27. Please change "polv(ADP ribose)" to --poly(ADP ribose)--

This certificate supersedes the Certificate of Correction issued April 13, 2010.

Signed and Sealed this

Thirteenth Day of July, 2010

David J. Kappos
*Director of the United States Patent and Trademark Office*

UNITED STATES PATENT AND TRADEMARK OFFICE
CERTIFICATE OF CORRECTION

PATENT NO. : 7,635,686 B2 Page 1 of 1
APPLICATION NO. : 10/264280
DATED : December 22, 2009
INVENTOR(S) : Phillips et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 566 days.

Signed and Sealed this

Twenty-first Day of December, 2010

David J. Kappos
*Director of the United States Patent and Trademark Office*

```
                        SEQUENCE LISTING

<160> NUMBER OF SEQ ID NOS: 8

<210> SEQ ID NO 1
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 1 gggtgg                                                                    6

<210> SEQ ID NO 2
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 2 gggagg                                                                    6

<210> SEQ ID NO 3
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 3 ccaccc                                                                    6

<210> SEQ ID NO 4
<211> LENGTH: 3
<212> TYPE: DNA
<213> ORGANISM: Artificial Sequence
<220> FEATURE:
<223> OTHER INFORMATION: Synthetic Oligonucleotide

<400> SEQUENCE: 4 gtg                                                                       3

<210> SEQ ID NO 5
<211> LENGTH: 6
<212> TYPE: DNA
```

```
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: 3'-Triethyleneglycol (TEG) Cholesteryl
      Synthetic Oligonucleotide

<400> SEQUENCE: 5 gggtgg                                                                   6

<210> SEQ ID NO 6
<211> LENGTH: 6
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: 3'-Triethyleneglycol (TEG) Cholesteryl
      Synthetic Oligonucleotide

<400> SEQUENCE: 6 gggagg                                                                   6

<210> SEQ ID NO 7
<211> LENGTH: 6
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: 3'-Triethyleneglycol (TEG) Cholesteryl
      Synthetic Oligonucleotide

<400> SEQUENCE: 7 ccaccc                                                                   6

<210> SEQ ID NO 8
<211> LENGTH: 3
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<223> OTHER INFORMATION: 3'-Triethyleneglycol (TEG) Cholesteryl
      Synthetic Oligonucleotide

<400> SEQUENCE: 8 gtg                                                                      3
```